United States Patent
Sanche et al.

(10) Patent No.: US 9,302,003 B2
(45) Date of Patent: Apr. 5, 2016

(54) COMPOSITIONS COMPRISING A RADIOSENSITIZER AND AN ANTI-CANCER AGENT AND METHODS OF USES THEREOF

(75) Inventors: Léon Sanche, Stoke (CA); Gabriel Charest, Sherbrooke (CA)

(73) Assignee: SOCPRA—SCIENCES SANTÉ ET HUMAINES, Sherbrooke (CA)

( * ) Notice: Subject to any disclaimer, the term of this patent is extended or adjusted under 35 U.S.C. 154(b) by 435 days.

(21) Appl. No.: 13/259,213

(22) PCT Filed: Apr. 26, 2010

(86) PCT No.: PCT/CA2010/000583
§ 371 (c)(1),
(2), (4) Date: Dec. 13, 2011

(87) PCT Pub. No.: WO2010/121368
PCT Pub. Date: Oct. 28, 2010

(65) Prior Publication Data
US 2012/0093918 A1    Apr. 19, 2012

Related U.S. Application Data

(60) Provisional application No. 61/172,482, filed on Apr. 24, 2009.

(51) Int. Cl.
*A61K 41/00* (2006.01)
*A61K 9/14* (2006.01)
*A61K 9/00* (2006.01)
(Continued)

(52) U.S. Cl.
CPC ............ *A61K 41/0038* (2013.01); *A61K 9/0019* (2013.01); *A61K 9/1271* (2013.01); *A61K 31/282* (2013.01); *A61K 33/24* (2013.01); *A61K 45/06* (2013.01); *Y10S 977/773* (2013.01); *Y10S 977/911* (2013.01)

(58) Field of Classification Search
None
See application file for complete search history.

(56) References Cited

U.S. PATENT DOCUMENTS

| | | | |
|---|---|---|---|
| 6,530,944 B2 * | 3/2003 | West et al. | 607/88 |
| 6,538,032 B1 * | 3/2003 | Namgoong et al. | 514/642 |
| 2005/0020869 A1 * | 1/2005 | Hainfeld et al. | 600/1 |

FOREIGN PATENT DOCUMENTS

| | | |
|---|---|---|
| EP | 1704870 | 9/2006 |
| WO | WO 0045845 | 8/2000 |

(Continued)

OTHER PUBLICATIONS

PM Kasili, T Vo-Dinh. "Photothermal Treatment of Human Carcinoma Cells Using Liposome-Encapsulated Gold Nanoshells." NanoBiotechnology, vol. 1, 2005, pp. 245-252.*

(Continued)

*Primary Examiner* — Isaac Shomer
(74) *Attorney, Agent, or Firm* — Goudreau Gage Dubuc; Julie Gauvreau

(57) ABSTRACT

A combination of an anti-cancer agent and a metal radiosensitizer potentiates the radiotherapy of cancer. Said anti-cancer agent is preferably cisplatin while the metal radiosensitizer is preferably gold nanoparticles. Both the anti-cancer agent and the metal radiosensitizer bind to DNA and potentiate the radiotherapy of cancer by synergistically increases the amount of double strand breaks induced by the radiation. The anti-cancer agent and the metal radiosensitizer may be encapsulated in liposomes.

20 Claims, 6 Drawing Sheets

(51) Int. Cl.
A61K 9/127 (2006.01)
A61K 31/282 (2006.01)
A61K 33/24 (2006.01)
A61K 45/06 (2006.01)

(56) References Cited

FOREIGN PATENT DOCUMENTS

| WO | WO 2004112590 | 12/2004 |
|---|---|---|
| WO | WO 2006037081 | 4/2006 |
| WO | WO 2008053484 | 5/2008 |

OTHER PUBLICATIONS

JE Parks. "The Compton Effect—Compton Scattering and Gamma Ray Spectrsocopy." Aug. 1, 2009, 32 pages, http://www.phys.utk.edu/labs/modphys/Compton%20Scattering%20Experiment.pdf, accessed Aug. 9, 2013.*
ISR, WO, Jul. 27, 2010.
Berdys, J. I. et al., "Damage to model DNA fragments from very low-energy (1< eV) electrons", J. Am. Chem. Soc., (2004), 126, 6441-6447.
Bose, R. N., "Biomolecular targets for platinum antitumor drugs", Mini-Rev. Med. Chem., (2002), 2, 103-111.
Boudaïffa, B., P. et al., "Cross sections for low-energy (10-50eV) electron damage to DNA", Radiat. Res., (2002),157, 227-234.
Boulikas, T., "Molecular mechanisms of cisplatin and its liposomally encapsulated form, Lipoplatin™", as a chemotherapy and antiangiogenesis drug. Cancer Therapy, (2007), 5: 349-376.
Brabec, V., "Platinum-based Drugs in cancer therapy", edited by LR. Kelland and N. Farrell, Humana Press Inc., Totowa, NJ, (2000), 37-61.
Caffo, "Radiosensitization with chemotherapeutic agents", Lung Cancer, (2001), S81-S90.
Cai, Z., et al., "Dosimetry of ultrasoft X-rays (1.56 keV AlKα) using radiochromatic films and color scanners", Phys. Med. Biol., (2003), 48: 4111-4124.
Charest G. et al., "Acta Neurochir", (2009), 151(6): 677-684.
Cho et al., "Chemoradiotherapy with or without consolidation chemotherapy using cisplatin and 5-fluorouracil in anal squamous cell carcinoma: Long term results of 31 patients", BMC Cancer, (2008), 8: 1-8.
Cuenca et al., "Emerging implications of nanotechnology on cancer diagnostics and therapeutics", Cancer (2006), 107(3): 459-466.
Eifel, P. J., "Concurrent chemotherapy and radiation therapy as the standard of care for cervical cancer", Nat. Clin. Pract. Oncol., (2006), 5: 248-255.
Fasman, G. D., "Handbook of Biochemistry and Molecular Biology", 3rd ed. CRC Press, Boca Raton, FL, (1995).
Guo et al., "Synergistic cytotoxic effect of different sized ZnO nanoparticles and daunorubicin against leukemia cancer cells under UV irradiation", Journal of Photochemistry and Photobiology b: Biology, (2008), 93: 119-126.
Harrington et al., "Phase I-II study on pegylated liposomal cisplatin (SPI-077tm) in patients with inoperable head and neck cancer", Annals of Oncology, (2001), 12: 493-496.
Hayat, M. A., "Colloid Gold, Principles, Methods and Applications", Academic Press, New York, (1989).

Hellman, S. et al., "Cancer: Principles and Practice of Oncology", edited by V. T. Devita, , 6th ed. Lippincott Williams and Wilkins, Philadelphia, PA, (2001).
Hostetler, M. J., et al., "Alkanethiolate gold cluster molecules with core diameter from 1.5 to 5.2 nm: core and monolayer properties as a function of core size", Langmuir, (1998),14: 17-30.
Johns H. E. et al., "The physics of Radiology", edited by H. Springfield, Charles C. Thomas Publisher, U. S. A. 1983.
Kies, M.S. et al., "Locally advanced head and neck cancer", Current Treatment Options in Oncology, 2(1): 7-13.
Kitada, N.,et al., "Factors affecting sensitivity to antitumor platinum derivatives of human colorectal tumor cell lines", Cancer Chemother. Pharmacol., (2008), 62: 577-584.
Knaebel et al., "Phase III trial of postoperative cisplatin, interferon alpha-2b and 5-FU combined with external radiation treatment versus 5-FU alone for patients with resected pancreatic adenocarcinoma—CapRI: Study protocol", BMC Cancer, (2005) 5: 37.
Kojima et al., "Preparation and characterization of complexes of liposomes with gold nanoparticles", Colloids and Surfaces B: Biointerfaces, (2008), 66: 246-252.
Kumar et al., "The role of to excited states in electron-induced DNA strand break formation: A time-dependent density functional theory study", J. Am. Chem. Soc., (2008),130: 2130-2131.
Liu et al., "Enhanched x-ray irradiation-induced cancer cell damage by gold nanoparticles treated by a new synthesis method of polyethylene glycol modification", Nanotechnology, (2008), 19: 295104 (5pp).
Meesungnoen, J., "Low-energy electron penetration range in liquid water", Radiat. Res., (2002),158: 657-660.
O'Reilly et al., "Cisplatin and irinotecan in upper gastrointestinal malignancies", Oncology, (2001), 15(3): 42-45.
Paasonen et al., "Gold nanoparticles enable selective light-induced contents release from liposomes". J. Control Release, (2007) 122: 86-93.
Pimblott S. M., et al., "Production of low-energy electrons by ionizing radiation". Rad. Phys. Chem., (2007), 76: 1244-1249.
Sanche L., "Radiation Induced Molecular Phenomena in Nucleic Acid, A comprehensive theoretical and experimental analysis series", vol. 5, edited by M.K. Shukla and J. Leszczynski, Springer, Netherland, (2008), 5:538-572.
Stopping power and range tables for electrons, Data from NIST website : http://physics.nist.gov/PhysRefData/Star/Text/ESTAR.html.
Zheng, Y., et al., Radiosensitization of DNA by gold nanoparticles irradiated with high-energy electrons. Radiat. Res., (2008), 169: 19-27.
Zheng, Y., et al., "Role of secondary low energy electrons in the concomitant chemoradiation therapy of cancer". Phys. Rev. Lett., (2008), 100: 198101-4.
Zheng, Y., et al., "Gold nanoparticles enhance DNA damage induced by anti-cancer drugs and radiation", Radiation Research, (2009), 172: 114-119.
Laverne et al., "Electron Energy-Loss Distributions in Solid, Dry DNA", Radiation Research, (1995), 141(2): 208-215.
Nikjoo et al., "The Auger effect in physical and biological research", Int. J. Radiat. Biol., (2008), 84(12): 1011-1026.
Pimblott et al., "Production of low-energy electrons by ionizing radiation", Radiation Physics and Chemistry, (2007), 76: 1244-1247.

* cited by examiner

US 9,302,003 B2

COMPOSITIONS COMPRISING A RADIOSENSITIZER AND AN ANTI-CANCER AGENT AND METHODS OF USES THEREOF

CROSS-REFERENCE TO RELATED APPLICATIONS

This application is a National Entry Application of PCT application no PCT/CA2010/000583 filed on Apr. 26, 2010 and published in English under PCT Article 21(2), which itself claims benefit of U.S. provisional application Ser. No. 61/172,482, filed on Apr. 24, 2009. All documents above are incorporated herein in their entirety by reference.

STATEMENT REGARDING FEDERALLY SPONSORED RESEARCH OR DEVELOPMENT

N.A.

FIELD OF THE INVENTION

The present invention relates to compositions comprising a radiosensitizer and an anti-cancer agent useful in the treatment of cancer. More specifically, the present invention is concerned with a metal radiosensitizer and an anti-cancer agent for increasing the amount of strand breaks in the DNA of a cell following radiotherapy.

BACKGROUND OF THE INVENTION

Cancer is a worldwide problem that afflicts millions of people each year. As such, finding new methods of treatments is of vital interest. Both chemotherapy and radiation therapy are used in the treatment of cancer. Radiation treatment has become a conventional part of cancer therapy and is used in approximately 60% of treatment regimens. The cytotoxic effect of radiation on cancer cells arises from the ability of radiation to cause breaks in one or both strands of the DNA molecules inside the cells. Cells in all phases of the cell cycle are susceptible to this effect. However, the DNA damage in cancer cells is more likely to be lethal because these cells are less capable of repairing their DNA. The side effects of radiation are similar to those of chemotherapy and occur for the same reason i.e., the damage of healthy cells and tissue. Thus, a shortcoming to radiotherapy is the destruction of normal, healthy tissue surrounding the tumor during treatment. Another shortcoming is that after cessation of treatment, recurrence of the tumor can and does occur. Recurrence of the tumor has been partly attributed to the presence of radioresistant hypoxic cells, and the enhancement of radiation doses to damage the hypoxic tumor tissue is often necessary. However, to save normal, healthy tissue, a reduction in the total radiation dose would be desirable. Obviously, these two factors are contradictory. Therefore, the use of certain drugs and chemicals that preferentially sensitize hypoxic tumor cells to radiation, radiosensitizers, are employed. Radiosensitizers normally are chemical agents that have the capacity to increase the lethal effects of radiation when administered in conjunction with radiation and there are a variety of radiosensitizers that act by more than one mechanism. Furthermore, in the treatment of cancer with radiation and chemotherapy, local tumor control is often improved when radiation is administered synchronously with the chemotherapeutic agent (21). This observation has been attributed to a super additive effect on tumor regression due to a synergistic interaction between the radiation and the drug. Nevertheless, despite the above improvements in cancer treatment, cancer remains difficult to treat and cells still become resistant to radiation therapy.

Thus, alternative methods and compositions which will increase the sensitivity of cancer cells to radiation therapy, thereby allowing for less exposure to toxic chemotherapeutic agents and radiation therapy, reduced side-effects and improved beneficial results, are still desirable. The present invention seeks to meet these and other needs.

The present description refers to a number of documents, the content of which is incorporated by reference in their entirety.

SUMMARY OF THE INVENTION

Accordingly, the present invention generally relates to new compositions, methods and uses for increasing the sensitivity of cancer cells to radiation therapy, for potentiating radiotherapy treatment and/or for increasing the amount of strand breaks in DNA in a cell (e.g., tumor cell).

It has been surprisingly discovered that metal radiosensitizers such as gold nanoparticles (GNP or AuNp) synergistically increase the anti-cancer activity of anti-cancer agents and of radiotherapy. It was established that by combining metal radiosensitizers with anti-cancer agents in radiotherapy, the number of DNA double strand breaks (DSB) and/or single strand breaks (SSB) could be increased up to ten-fold as compared to radiation alone. Without being limited to any theory, this synergistic effect could be due, among other things, to the higher density of low energy electrons and reactive species around the metal radiosensitizers and the weakening of the bonds adjacent to the anti-cancer agent located on or in close proximity to the DNA backbone.

Anti-cancer agent cisplatin was chemically linked to pGEM-3Zf plasmid DNA to produce a cisplatin-DNA complex. Gold nanoparticles which bind electrostatically to pure DNA were used as a metal radiosensitizer and were added to this complex. Dry films of pure plasmid DNA and DNA-cisplatin, DNA-gold nanoparticles and DNA-cisplatin-gold nanoparticles complexes were bombarded by 60 keV electrons. The yields of single and double strand breaks were measured as a function of exposure by electrophoresis. From comparison of yields generated by the different types of films, it was found that the binding of only one gold nanoparticle to a plasmid-cisplatin complex containing 3,197 base pairs increases by a factor of 4 the efficiency of chemotherapeutic agent cisplatin to produce double strand breaks in irradiated DNA. Furthermore, adding two cisplatin molecules and one gold nanoparticle to DNA enhances by an order of magnitude radiation-induced double strand breaks. A number of phenomena could contribute to this huge enhancement, including the higher density of low energy electrons and reactive species around the radiosensitizers and the weakening of bonds adjacent to cisplatin in the DNA backbone.

Radiosensitizer and anti-tumor agent loaded-liposomes were also administered in vivo to a rat cancer model.

Accordingly, in an embodiment, the present invention provides a method of treating cancer comprising administering to a subject in need thereof a composition comprising an effective amount of an anti-cancer agent and a metal radiosensitizer and treating said patient with radiotherapy. The administration of the metal radiosensitizer and anti-cancer agent provides for a synergistic effect in increasing the amount of DNA strand breaks in cancer cells when said patient is treated with radiotherapy.

In a specific embodiment, the cancer is glioma. In a specific embodiment when the drug is cisplatin, the cancer is of a type for which this drug has been approved by the FDA. Without being so limited, the cancer is bladder cancer (e.g., that cannot be treated with surgery or radiotherapy alone), ovarian cancers (e.g., that has metastasized and not improved with other drugs, in patients who have already had surgery or radiotherapy), testicular cancer (e.g., in patients who have already had surgery or radiotherapy), squamous cell carcinoma of the head and neck (SCCHN) (e.g., locally advanced that cannot be treated with surgery), cervical cancer (e.g., late-stage that cannot be treated with surgery or radiotherapy alone), malignant mesothelioma (e.g., that cannot be treated with surgery), non-small cell lung cancer (NSCLC) (e.g., locally advanced, advanced, or metastatic that cannot be treated with surgery). In addition to the uses that have been approved by the FDA, cisplatin is sometimes used alone or with other drugs to treat other types of cancer.

In a related aspect, the present invention provides a method of potentiating radiotherapy treatment comprising administering to a subject in need thereof an effective amount of an anti-cancer agent and of a metal radiosensitizer prior to radiotherapy.

In another aspect, the present invention provides a method of enhancing radiosensitivity of a cell population comprising exposing said cell population to an effective amount of a metal radiosensitizer and of an anti-cancer agent.

In yet another aspect, the present invention provides a method of increasing the amount of strand breaks in DNA in a cell comprising: contacting said cell with an effective amount of an anti-cancer agent and of a metal radiosensitizer; and submitting said cell to radiotherapy.

In a specific embodiment, the radiotherapy comprises ionizing radiation. In another embodiment, the ionizing radiation comprises low energy electrons. In another embodiment, said anti-cancer agent is a platinum compound or a derivative thereof. In another embodiment, said platinum compound is cisplatin, carboplatin, oxaliplatin, a derivative thereof or a combination thereof. In another embodiment, said platinum compound is cisplatin. In another embodiment, said metal radiosensitizer comprises nanoparticles of an inert metal. In another embodiment, said metal radiosensitizer comprises gold nanoparticles. In another embodiment, said gold nanoparticles have an average diameter of between 1 and 60 nanometers. In another embodiment, said strand breaks are double strand breaks. In another embodiment, said anti-cancer agent and said metal radiosensitizer are administered simultaneously. In another embodiment, said anti-cancer agent and said metal radiosensitizer are administered separately.

In another embodiment, said anti-cancer agent and said metal radiosensitizer are encapsulated in liposomes. In another embodiment, a majority of said liposomes have a diameter of less than 400 nm. In another embodiment, a majority of said liposomes have a diameter between about 100 and about 150 nm. In another embodiment, said liposomes are coated with Polyethylene glycol (PEG). In another embodiment, said liposomes preferentially target cancer cells. In another embodiment, said liposomes comprise dipalmitoyl phosphatidyl glycerol (DPPG), soy phosphatidyl choline, cholesterol and methoxy-polyethylene glycol-distearoyl phosphatidyl-ethanolamine (mPEG2000-DSPE). In another embodiment, said liposomes comprise dipalmitoylphosphatidylcholine (DPPC), 3β-[N—(N',N'-dimethylaminoethane)-carbamoyl]-cholesterol (DC-Chol) and Dioleoyl Phosphatidylethanolamine (DOPE). In a further embodiment, said liposomes comprise polyethylene glycol (PEG). In another embodiment, said liposomes have a mean diameter of between about 70 nm to 152 nm. In another embodiment, said liposomes further comprise a stabilizer. In another embodiment, said stabilizer is polyacrylamide, polyvinyl, dextrose, D-glucose and dithiolated diethylenetriaminepentaacetic acid (DTDTPA).

In another aspect, the present invention provides radiosensitizing compositions comprising an effective amount of an anti-cancer agent, a metal radiosensitizer and a suitable pharmaceutical carrier. In an embodiment, the radiosensitizing composition potentiates the amount of DNA strand breaks in cells during radiotherapy.

In another aspect, the present invention provides the use of an effective amount of a metal radiosensitizer and an anti-cancer agent for the treatment of cancer in a subject in need thereof. The present invention provides the use of a composition comprising a metal radiosensitizer and an anti-cancer agent for the preparation of a medicament for the treatment of cancer.

In another aspect, the present invention provides the use of an effective amount of a metal radiosensitizer and of an anti-cancer agent for (a) enhancing radiosensitivity of a cell population, or for (b) potentiating radiotherapy treatment; or (c) increasing the amount of strand breaks in DNA in a cell during radiotherapy.

In another aspect, the present invention provides a use of an effective amount of a metal radiosensitizer and of an anti-cancer agent in the manufacture of a medicament for (a) enhancing radiosensitivity of a cell population, or for (b) potentiating radiotherapy treatment; or (c) increasing the amount of strand breaks in DNA in a cell during radiotherapy.

In a specific embodiment, said radiotherapy comprises ionizing radiation. In another specific embodiment, said ionizing radiation comprises low energy electrons. In another specific embodiment, said anti-cancer agent is a platinum compound or a derivative thereof. In another specific embodiment, said platinum compound is cisplatin, carboplatin, oxaliplatin, a derivative thereof or a combination thereof. In another specific embodiment, said platinum compound is cisplatin. In another specific embodiment, said metal radiosensitizer comprises nanoparticles of an inert metal. In another specific embodiment, said metal radiosensitizer comprises gold nanoparticles. In another specific embodiment, said gold nanoparticles have an average diameter of between 1 and 60 nanometers. In another specific embodiment, said strand breaks are double strand breaks. In another specific embodiment, said anti-cancer agent and said metal radiosensitizer are adapted for simultaneous administration. In another specific embodiment, said anti-cancer agent and said metal radiosensitizer are adapted for separate administration.

In another specific embodiment of said uses, said anti-cancer agent and said metal radiosensitizer are encapsulated in liposomes. In another specific embodiment, a majority of said liposomes have a diameter of less than 400 nm. In another specific embodiment, a majority of said liposomes have a diameter of between about 100 nm and about 150 nm. In another specific embodiment, said liposomes are coated with polyethylene glycol (PEG). In another specific embodiment, said liposomes are adapted to preferentially target cancer cells. In another specific embodiment, said liposomes comprise dipalmitoylphosphatidylcholine (DPPC), 3β-[N—(N',N'-dimethylaminoethane)-carbamoyl]-cholesterol (DC-Chol), Dioleoyl Phosphatidylethanolamine (DOPE) and polyethylene glycol (PEG). In another specific embodiment, said liposomes comprise dipalmitoyl phosphatidyl glycerol (DPPG), soy phosphatidyl choline, cholesterol and methoxy-polyethylene glycol-distearoyl phosphatidyl-ethanolamine (mPEG$_{2000}$-DSPE). In another specific embodiment, said liposomes have a mean diameter of between about 70 nm and about 152 nm. In another specific embodiment, said liposomes further comprise a stabilizer. In another specific embodiment, the stabilizer comprises polyacrylamide, polyvinyl, dextrose, D-glucose or dithiolated diethylenetriaminepentaacetic acid (DTDTPA).

In another aspect, the present invention provides a use of a composition comprising a metal radiosensitizer and an anti-cancer agent for potentiating radiotherapy treatment.

In another aspect, the present invention provides a use of an effective amount of a metal radiosensitizer and an anti-cancer agent for increasing the amount of DNA strand breaks in a cell population.

In another embodiment, the present invention relates to the use of an effective amount of a metal radiosensitizer and an anti-cancer agent for synergistically increasing the amount of DNA breaks in a cell population when treated with ionizing radiation.

In another aspect, the present invention provides a use of an effective amount of a metal radiosensitizer and an anti-cancer agent for enhancing radiosensitivity of a cell population.

In another aspect, the present invention concerns a composition comprising a metal radiosensitizer and an anti-cancer agent for use in potentiating the effect of radiotherapy.

In another aspect, the present invention concerns a pharmaceutical composition comprising a metal radiosensitizer and an anti-cancer agent for use in (a) potentiating the effect of radiotherapy; (b) enhancing radiosensitivity of a cell population; or (c) increasing the amount of DNA strand breaks in a cell population.

In another aspect, the present invention concerns a pharmaceutical composition comprising an effective amount of an anti-cancer agent, a metal radiosensitizer and a pharmaceutically acceptable carrier.

In a specific embodiment of the compositions, said radiotherapy comprises ionizing radiation. In another specific embodiment, said ionizing radiation comprises low energy electrons. In another specific embodiment, said anti-cancer agent is a platinum compound or a derivative thereof. In another specific embodiment, said platinum compound is cisplatin, carboplatin, oxaliplatin, a derivative thereof or a combination thereof. In another specific embodiment, said platinum compound is cisplatin. In another specific embodiment, said metal radiosensitizer comprises nanoparticles of an inert metal. In another specific embodiment, said metal radiosensitizer comprises gold nanoparticles. In another specific embodiment, said gold nanoparticles have an average diameter of between 1 nanometers and 60 nanometers. In another specific embodiment, said strand breaks are double strand breaks. In another specific embodiment, said anti-cancer agent and said metal radiosensitizer are adapted for simultaneous administration. In another specific embodiment, said anti-cancer agent and said metal radiosensitizer are adapted for separate administration.

In another specific embodiment of the compositions, said anti-cancer agent and said metal radiosensitizer are encapsulated in liposomes. In another specific embodiment, a majority of said liposomes have a diameter of less than 400 nm. In another specific embodiment, a majority of said liposomes have a diameter of between about 100 and about 150 nm. In another specific embodiment, said liposomes are coated with polyethylene glycol (PEG). In another specific embodiment, said liposomes are adapted to preferentially target cancer cells. In another specific embodiment, said liposomes comprise dipalmitoylphosphatidylcholine (DPPC), 3β-[N—(N',N'-dimethylaminoethane)-carbamoyl]-cholesterol (DC-Chol), Dioleoyl Phosphatidylethanolamine (DOPE) and polyethylene glycol (PEG). In another specific embodiment, said liposomes comprise dipalmitoyl phosphatidyl glycerol (DPPG), soy phosphatidyl choline, cholesterol and methoxy-polyethylene glycol-distearoyl phosphatidyl-ethanolamine (mPEG$_{2000}$-DSPE). In another specific embodiment, said liposomes have a mean diameter of between about 70 nm and about 152 nm. In another specific embodiment, said liposomes further comprise a stabilizer. In another specific embodiment, said stabilizer comprises polyacrylamide, polyvinyl alcohol (PVA), dextrose, D-glucose or dithiolated diethylenetriaminepentaacetic acid (DTDTPA).

In accordance with another aspect of the present invention, there is provided a pharmaceutical composition comprising a metal radiosensitizer and an anti-cancer agent for use in potentiating the effect of radiotherapy.

In accordance with another aspect of the present invention, there is provided a pharmaceutical composition comprising a metal radiosensitizer and an anti-cancer agent for use in enhancing radiosensitivity of a cell population.

In accordance with another aspect of the present invention, there is provided a pharmaceutical composition comprising a metal radiosensitizer and an anti-cancer agent for use in increasing the amount of DNA strand breaks in a cell population.

In another aspect, the present invention relates to a method of reducing the toxicity of an anti-cancer therapy comprising administering, before the radiotherapy treatment, to a subject in need thereof an effective amount of a radiosensitizer in combination with (simultaneously with (separately or together), or sequentially) an anti-cancer agent.

In an embodiment, the above-mentioned anti-cancer agent of the present invention is an anti-cancer agent which binds to DNA. In another embodiment, the anti-cancer agent is an alkylating agent. In a further embodiment, the anti-cancer agent is a platinum compound or derivative thereof. In yet a further embodiment, the platinum compound of the present invention is cisplatin, carboplatin, oxaliplatin, derivatives thereof or combinations thereof. In an embodiment, the above-mentioned platinum compound is cisplatin.

In an embodiment, the above-mentioned metal radiosensitizer comprises nanoparticles of at least one inert metal. In an embodiment, the at least one inert metal is gold. In an embodiment, the nanoparticles are between about 1 and about 60 nanometers. "About" as used herein refers to a difference of 0.2 or less.

In an embodiment, in the compositions and methods of the present invention, the above-mentioned DNA breaks caused by the synergistic effect of the metal radiosensitizer and anti-cancer agent are double strand breaks.

In a particular embodiment of the present invention, the anti-cancer agent and metal radiosensitizer are administered simultaneously. Alternatively, the anti-cancer agent and metal radiosensitizer can be administered separately as long as both the agent and the radiosensitizer are administered prior to radiotherapy and in such a way that both are present in the same cells at the time of irradiation, so as to provide a synergistic effect on the amount of strand breaks to DNA.

In another particular embodiment of the present invention, the above-mentioned anti-cancer agent and metal radiosensitizer are encapsulated in liposomes.

In an embodiment, the liposomes are less than 400 nm in size. In another embodiment, the liposomes are between 100 and 150 nm in size. In a further embodiment, the liposomes are coated with Polyethylene glycol (PEG). In another embodiment, the liposomes have a mean diameter of between about 70 nm and 152 nm size.

In another specific embodiment, the liposomes comprise dipalmitoylphosphatidylcholine (DPPC), 3β-[N—(N',N'- dimethylaminoethane)-carbamoyl]-cholesterol (DC-Chol), dioleoyl Phosphatidylethanolamine (DOPE). In more specific embodiments, the liposomes comprise PEG. PEG can be administered alone or attached to another lipids such as but not limited to DPPC and/or 1,2-distearoyl-sn-glycero-3-phosphoethanolamine-N (DSPE) and polyethylene glycol PEG.

In a particular embodiment, the liposomes comprise dipalmitoyl phosphatidyl glycerol (DPPG), soy phosphatidyl choline, cholesterol and methoxy-polyethylene glycol-distearoyl phosphatidyl-ethanolamine (mPEG2000-DSPE). Preferably, the liposomes used in accordance with the present invention have a mean diameter of between about 70 nm and 152 nm size and are similar to the liposomes used for the Lipoplatin™ formulation.

In an embodiment, the compositions and liposomes of the present invention preferentially target cancer cells over healthy cells.

The present invention also provides a kit or package comprising the above-mentioned agent or pharmaceutical compositions. Such kit may further comprises, for example, instructions for the prevention and/or treatment of cancer, containers, devices for administering the agent/composition, etc.

More specifically, in accordance with the present invention, there is provided a kit comprising a metal radiosensitizer and an anti-cancer agent and instructions for use in (a) increasing the amount of strand breaks in DNA in a cell; (b) potentiating the effect of radiotherapy; or (c) enhancing radiosensitivity of a cell population.

In a specific embodiment of the kit, said radiosensitizer is gold or platinum nanoparticles and said anti-cancer agent is cisplatin, carboplatin, oxaliplatin or a derivative thereof. In another specific embodiment, said radiosensitizer is gold nanoparticles and said anti-cancer agent is cisplatin.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
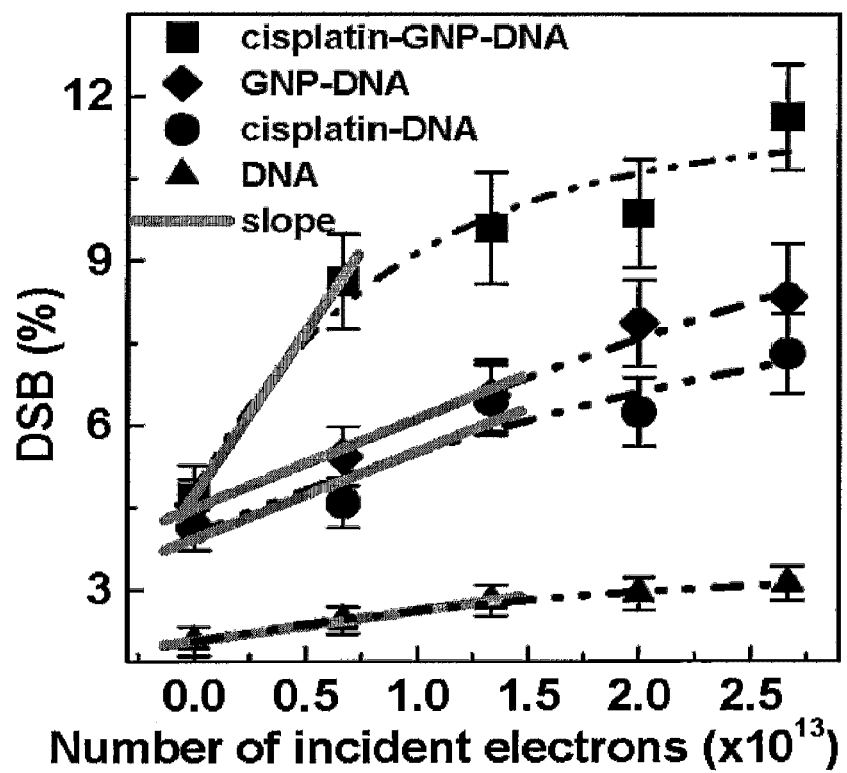
FIG. 1 shows a dose response curve of DSB induced by a 60 keV electron impact on 2900 nm films of pure DNA (▲), cisplatin-plasmid (●), gold nanoparticles (GNP)-plasmid (♦) and cisplatin-GNP-plasmid (■) complexes in ratios of 2:1, 1:1, and 2:1:1, respectively. The dash lines are exponential fits.

The articles "a," "an" and "the" are used herein to refer to one or to more than one (i.e., to at least one) of the grammatical objects of the article.

The term "including" and "comprising" are used herein to mean, and are used interchangeably with, the phrases "including but not limited to" and "comprising but not limited to".

The term "such as" is used herein to mean, and is used interchangeably with, the phrase "such as but not limited to".

As used herein the term "cancer" is intended to include any form of cancer or tumors. Non-limiting examples of cancers include brain cancer (e.g., glioma), gastric cancer, pancreatic cancer, non-small cell lung cancer, small cell lung cancer, prostate cancer, colon cancer, non-Hodgkin's lymphoma, sarcoma, testicular cancer, acute non-lymphocytic leukemia and breast cancer.

The methods, compositions formulations and uses described herein are suitable for both humans and animals, preferably mammals.

Thus, as used herein, the term "subject" in the context of the present invention relates to any mammal including a mouse, rat, pig, monkey and horse. In a specific embodiment, it refers to a human. A "subject in need thereof" or a "patient" in the context of the present invention is intended to include any subject that will benefit or that is likely to benefit from the compositions and pharmaceutical compositions of the present invention. Thus, the "subject" of the present invention is a subject suffering from any form of cancer that might benefit from a combination of radiotherapy and chemotherapy and in particular that could benefit from an increase in strand breaks of DNA in the cancer cell population. The subject may suffer from a cancer of any stage such that it could be an early non invasive cancer or could be a late stage cancer that has already progressed to form metastases in the body.

The terms "treat/treating/treatment" as used herein, refers to eliciting the desired biological response, i.e., a therapeutic effect. Hence "treat/treating/treatment" in the expression "treating cancer" is meant to refer for example to any partial or complete reduction in tumor size and/or an arrest or reduction in tumor growth or a delay in the apparition of resistant hypoxic tumor cells. The terms "treat/treating/treatment" further include an increase in cancer cells death due to an increase in the number of strand breaks in DNA of tumor cells provided by the synergistic action of the metal radiosensitizer and anti-cancer agent of the present invention.

In addition, the therapeutic effect may comprise an amelioration of one or more other symptoms associated with cancer (anaemia, chronic fatigue, nausea, loss of bone mass, progressive loss of both fat and skeletal muscle, refractoriness of weight loss to increased nutritional input, elevated resting energy expenditure (REE), decreased protein synthesis, altered carbohydrate metabolism, hyper-catabolism/increased degradation of muscle via the ATP-ubiquitin-proteasome pathway of proteolysis and of adipose tissue via lipolysis, asthenia, etc.) and/or an increased survival time of the affected subject, following administration of a pharmaceutical composition of the present invention.

1. Anti-Cancer Agents

The anti-cancer agents of the present invention comprise anti-cancer agents that directly cross-link nucleic acids, specifically DNA and are envisaged to facilitate DNA damage leading to a synergistic, antineoplastic combination with the metal radiosensitizer and radiotherapy (e.g., alkylating agents). Non-limiting examples of anti-cancer agents include platinum-based anti-cancer agents which are thought to function as cell cycle inhibitors by binding to DNA, i.e., acting as alkylating agents of DNA.

Non-limiting examples of platinum compounds which may be used in accordance with the present invention include cisplatin, carboplatin and oxaliplatin, or derivatives thereof or combinations thereof. Non-limiting examples of derivatives include conventional platinum compounds in which the Pt atom is replaced by rutherium or palladium. Other examples include: $(CPA)_2Pt(DOLYM)$ and $(DACH)Pt(DOLYM)$ cisplatin (Choi et al., Arch. Pharmacol Res. 22(2):151-156, 1999), Cis-$(PtCl_2(4,7-H-5-methyl-7-oxo)1,2,4(triazolo(1,5-a)pyrimidine)_2)$ (Navarro et al., J. Med. Chem. 4i(3):332-338, 1998), $(Pt(cis-1,4-DACH)(trans-Cl_2)(CBDCA))$.MeOH cisplatin (Shamsuddin et al., Inorg. Chem. 36(25):5969-5971, 1997), 4-pyridoxate diamine hydroxy platinum (Tokunaga et al., Pharm. Sci. 3(7):353-356, 1997), Pt(II).Pt(II) ($Pt_2(NHCHN(C(CH_2)(CH_3)))_4$) (Navarro et al., Inorg. Chem. 35(26):7829-7835, 1996), 254-S cisplatin analogue (Koga et al., Neurol. Res. 15(3):244-247, 1996), trans,cis-$(Pt(OAc)_2I_2(en))$ (Kratochwil et al., J. Med. Chem. 39(13):2499-2507, 1996), cis-1,4-diaminocyclohexane cisplatin analogues (Shamsuddin et al., J. Inorg. Biochem. 61 (4):291-301, 1996), 5' orientational isomer of cis-$(Pt(NH_3)(4-aminoTEMP-O)\{d(GpG)\})$ (Dunham & Lippard, J. Am. Chem. Soc. 117(43): 10702-12, 1995), chelating diamine-bearing cisplatin analogues (Koeckerbauer & Bednarski, J. Pharm. Sci. S4(7):819-23, 1995), (ethylenediamine)platinum(II) complexes (Pasini et al., J. Chem. Soc, Dalton Trans. 4:579-85, 1995), CI-973 cisplatin analogue (Yang et al., Int. J. Oncol. 5(3):597-602, 1994), cis-diamminedichloroplatinum(II) and its analogues cis-1,1-cyclobutanedicarbosylato(2R)-2-methyl-1,4-butane-diam-mineplatinum(H) and cis-diammine(glycolato)platinum (Claycamp & Zimbrick, J. Inorg. Biochem., 26(4):257-67, 1986; Fan et al., Cancer Res. 48(11):3135-9, 1988; Heiger-Bernays et al., Biochemistry 29(36):8461-6, 1990; Kikkawa et al., J. Exp. Clin. Cancer Res. 72(4):233-40, 1993; Murray et al., Biochemistry 37(47): 11812-17, 1992; Takahashi et al., Cancer Chemother. Pharmacol. 33(1):31-5, 1993), cis-amine-cyclohexylamine-dichloroplatinum(II) (Yoshida et al., Biochem. Pharmacol. 48(A):193-9, 1994), gem-diphosphonate cisplatin analogues (FR 2683529), (meso-1,2-bis(2,6-dichloro-4-hydroxyplenyl)ethylenediamine)dichloroplatinum(II) (Bednarski et al., J. Med. Chem. 35(23):4479-85, 1992), trans-diamminedichloroplatinum(II) and cis-$(Pt(NH_3)_2(N_3-cytosine)Cl)$ (Bellon & Lippard, Biophys. Chem. 35(2-3): 179-88, 1990), 3H-cis-1,2-diaminocyclohexanedichloroplatinum(II) and 3H-cis-1,2-diaminocyclohexanemalonato-platinum(II) (Oswald et al., Res. Commun. Chem. Pathol. Pharmacol. 54(I):41-58, 1989), diaminocarboxylatoplatinum (EPA 296321), aminoalkylaminoanthraquinone-derived cisplatin analogues (Kitov et al., Eur. J. Med. Chem. 23(4):381-3, 1988), spiroplatin, carboplatin, iproplatin and JM40 platinum analogues (Schroyen et al., Eur. J. Cancer Clin. Oncol. 24(8): 1309-12, 1988), bidentate tertiary diamine-containing cisplatinum derivatives (Orbell et al., Inorg. Chim. Acta 752(2): 125-34, 1988), platinum(II), platinum(IV) (Liu & Wang, Shandong Yike DaxueXuebao 2¥(1):35-41, 1986), cis-diammine(1,1-cyclobutanedicarboxylato-)platinum(II) (carboplatin, JM8) and ethylenediamine-malonatoplatinum(II) (JM40) (Begg et al., Radiother. Oncol. 9(2): 157-65, 1987), JM8 and JM9 cisplatin analogues (Harstrick et al., Int. J. Androl. 10(1); 139-45, 1987), $(NPr_4)_2((PtCL_4).cis-(PtCl_2—(NH_2Me)_2))$ (Brammer et al., J. Chem. Soc, Chem. Commun. 5:443-5, 1987), aliphatic tricarboxylic acid platinum complexes (EPA 185225), cis-dichloro(amino acid)(tert-butylamine)platinum(II) complexes (Pasini & Bersanetti, Inorg. Chim. Acta 107(A):259-67, 1985), Polynuclear Platinum BBR3464, BBR3571, and BBR3610 (Billecke C. et al., Neuro-Oncol 8(3):215-26, 2006).

It should be understood that combinations of two or more anti-cancer agents can be used in accordance with the present invention as long as 1) at least one of the anti-cancer agents has a synergistic effect with the metal radiosensitizer and increases the number of strand breaks in cells DNA during radiotherapy; or 2) a combination of the at least one anti-cancer agent with the metal radiosensitizer enables the anti-cancer agent to be administered at a lower concentration while achieving a similar therapeutic effect (e.g., single and/or single strand breaks, survival time, etc.) during radiotherapy as would a higher dose of the anti-cancer agent not administered in combination with the metal radiosensitizer.

2. Radiation Therapy

Radiation therapy (also called radiotherapy) comprises the use of ionizing radiation to kill cancer cells and shrink tumors. Radiation therapy can be administered externally via external beam radiotherapy (EBRT) or internally via brachytherapy. Thus, radiation therapy is the medical use of ionizing radiation as part of cancer treatment to control malignant cells. Most common cancer types can benefit from a combination of radiotherapy and chemotherapy. Radiotherapy works by destroying the cancer cells (and by damaging their DNA) in the treated area.

Ionizing radiation consists of subatomic particles or electromagnetic waves that are energetic enough to detach electrons from atoms or molecules, ionizing them. The occurrence of ionizing events depends on the energy of the impinging individual particles or waves, and not on their number. An intense flood of particles or waves will not cause ionization if these particles or waves do not carry enough energy to be ionizing. Roughly speaking, particles or photons with energies above a few electron volts (eV) are ionizing. Electrons, x rays, gamma rays or atomic ions may be used in radiation therapy to treat malignant tumors (cancer). Energies of the order of MeVs is usually used in conventional radiotherapy. This high energy radiation, after interaction with matter (Compton effect), produces slow electrons that produce low energy electrons. For example, one photon of 1 MeV will produces near 40,000 low energy electrons. A total energy of 60 eV of radiation is believed to represent what is generally used in conventional radiotherapy.

Radiotherapy treatment can cure cancers and can also reduce the chance of a cancer coming back after surgery. It may be used to reduce cancer symptoms. Radiation therapy is commonly applied to the cancerous tumor. The radiation fields may also include the draining of lymph nodes if they are clinically or radiologically involved with the tumor or if there is a potential risk of subclinical malignant spread. It is necessary to include a margin of normal tissue around the tumor to allow for uncertainties in daily set-up and internal tumor motion. These uncertainties can be caused by internal movement (for example, respiration and bladder filling) and movement of external skin marks relative to the tumor position. To spare normal tissues (such as skin or organs through which radiation must pass in order to treat the tumor), shaped radiation beams are conventionally aimed from several angles of exposure to intersect at the tumor, providing a much larger absorbed dose there than in the surrounding, healthy tissue.

There are different types of radiotherapy machines, which work in slightly different ways. The number and duration of the radiotherapy sessions depend on the type of cancer and where it is located in the body. A superficial skin cancer may need only a few short treatments, whereas a cancer deeper in the body may need more prolonged treatment. Patients usually have external radiotherapy in small doses—each dose is called a fraction—usually five days in a row, from Monday to Friday, so normal tissue has a chance to recover from the treatment during the weekend. Accordingly, in an embodiment, the compositions of the present invention are administered daily prior to radiotherapy. The time of administration will depend on the specific formulation and on the time necessary for the anti-cancer agent and metal radiosensitizer to reach the target cells. The time of administration will be chosen so as to provide the optimal concentration of anti-cancer agent and metal radiosensitizers at the time of irradiation.

3. Radiosensitizers

Radiosensitizers are drugs that make cancer cells more sensitive to the effects of radiation therapy. The radiosensitizers used in the present invention are metal nanoparticles, preferably inert metal nanoparticles. The metal radiosensitizers of the present invention, when irradiated near an anti-cancer agent which is located on or in the proximity of the DNA, cause an increase in single and double strand breaks in DNA, a lethal type of damage, as compared to that caused by the anti-cancer agent alone. Non-limiting examples of metal radiosensitizers that could be used in accordance with the present invention include metals, preferably inert metals such as platinum, gold, iridium, osmium, palladium, rhodium, zinc, chromium, copper, silver, cobalt, nickel and ruthenium. The greater the atomic number, the better is the interaction with radiation. Toxic metals such as mercury and lead have a useful atomic mass but should not be used in accordance with the present invention. Other useful metals, although less preferred because of their small atomic number, include iron. Preferred inert metals are gold and platinum. Thus, in a preferred embodiment, the metal radiosensitizer comprises nanoparticles made of an inert metal, such that its administration to a subject does not cause any important immune reaction or adverse side effect. For example, gold nanoparticles are preferred because they are known to be inert in mammals, having long been used to treat rheumatoid arthritis. Without being tied to any particular theory, it is believed that when gold nanoparticles are irradiated near the DNA with an anti-cancer agent, preferably a platinum anti-cancer agent, they synergistically cause an increase in DNA double breaks, as compared to the amount of DNA double breaks caused by 1) radiation alone; 2) radiation and gold nanoparticles; or 3) radiation combined with the anti-cancer agent.

In a specific embodiment, the composition of the present invention may comprise additional elements for increasing biocompatibility of the metal particles for example. Non-limiting examples of such elements include elements of the class of halogens such as bromide or iodine.

4. Formulation and Administration

The pharmaceutical composition may further comprise a pharmaceutically acceptable carrier or excipient. As used herein "pharmaceutically acceptable carrier" or "excipient" includes any and all solvents, buffers, dispersion media, coatings, antibacterial and antifungal agents, isotonic and absorption delaying agents and the like that are physiologically compatible. The carrier is selected for administration by the selected route of administration. The use of such media and agents for pharmaceutically active substances is well known in the art (Rowe et al., Handbook of pharmaceutical excipients, 2003, 4$^{th}$ edition, Pharmaceutical Press, London UK). Except insofar as any conventional medium or agent is incompatible with the active compounds (i.e., the metal radiosensitizer and the anti-cancer agent), use thereof in the pharmaceutical compositions of the invention is contemplated.

Non-limiting pharmaceutically suitable materials that may be incorporated in pharmaceutical preparations of the present invention include solubilizing/diluting agents, antioxidants, enteric coatings, absorption enhancers, pH adjusting agents and buffers, dispersing agents, coatings, antibacterial and antifungal agents, absorption delaying agents, osmolarity adjusters, isotonic agents, preservative agents, stabilizers (e.g., radiosensitizer stabilizer and/or anti-cancer stabilizer), surfactants, thickening agents, solvents, co-solvents, emollients, coloring agents, wetting agents and ligands/pilote/targeting molecules. Methods for preparing appropriate formulations are well known in the art (see e.g., Hendrickson, 2005).

Solubilizing agents useful for the present invention encompass polyoxyethylene-sorbitan-fatty acid esters, polyoxyethylene fatty acid esters, PEG glyceryl fatty acid esters, propylene glycol mono- or di-fatty acid esters, sorbitan fatty acid esters, polyoxyethylene-polyoxypropylene co-polymers, glycerol triacetate, monoglycerides, acetylated monoglycerides, polysorbate glycerol fatty acid esters, acetylated esters of fatty acids, acacia, carbomer copolymer, carbomer interpolymer, cholesterol, diethanolamine aluminum monostearate, carboxy methyl cellulose, sodium desoxycholate, egg yolk phospholipid, hydrolyzed gelatin, lecithin, lanolin alcohols, poloxamer, povidone, sodium dodecyl sulphate, sorbitol, oils such as vegetable oils or animal oils (see relevant sections of USP-NF). Non-limiting examples of vegetable oils include canola, corn, flax seeds, cotton seeds, soybean, walnut, pine nut, peanut, grape seed, sunflower, safflower, olive, coconut, palm oil, etc. . . . ). Non-limiting examples of animal oils include fish, seal oil and castor oil. In more specific embodiments, they include any polysorbate including polysorbates 20, 21, 40, 60, 61, 65, 80, 81 and 85; Brij™ (polyoxyethyleneglycol alkyl ether having a polar side of 10 to 100 monomers) and Cremophor™ (e.g., Cremophor™ EL (derivative of castor oil and ethylene oxide)); Cremophor™ A6 (Polyethylene glycol 260 mono(hexadecyl/octadecyl) ether and 1-octadecanol) and Cremophor™ A25 (polyethylene glycol 1100 mono(hexadecyl/octadecyl)ether).

The solubilizers containing polyoxyethylene chains such as polysorbates, PEG, and Brij™ are susceptible to formation of peroxides by radicalar reactions catalyzed by light and oxygen. Non-limiting examples of solubilizers include PEG400, Cremophor™ EL, polysorbate 60 and polysorbate 80.

Antioxidants useful for formulations of the present invention include plant extracts (i.e., fruit, vegetable and/or leguminous extracts), algae extracts, microorganisms extracts such as yeast extracts and their derivatives, ferments, proteolysis hydrolysates, peptides, animal derivative extracts and synthetic compounds. More particularly, such ingredients include ethylbisiminomethylguaiacol manganese chloride; dipalmitoyl hydroxyproline, dimethylmethoxy chromanol; bioflavonoid hesperidin olive leaf extract, ubiquinone, super-oxide dismutase, flavanols, isoflavones, furfuryladenine, panthenol, lipoic acid, niacinamide, melatonin, catalase, glutathione, polyphenols, cysteine, allantoin, kinetin, squalane, grape seed extract and camellia sinensis extract, ascorbic acid and its derivatives (e.g., ascorbyl palmitate, magnesium ascorbyl phosphate, sodium ascorbyl phosphate), vitamin E and its derivatives (e.g., α-tocopherol, δ-tocopherol, γ-tocopherol, tocopheryl acetate, a hydrophilic vitamin E analog such as 6-hydroxy-2,5,7,8-tetramethylchroman-2-carboxylic acid (Trolox™), alpha-tocopherol acetate, alpha-tocopheryl polyethylene glycol succinate, alpha-tocopherol palmitate), butylated hydroxytoluene (BHT), butylated hydroxyanisole (BHA), hypophosphorous acid, monothioglycerol, potassium metabisulfite, propyl gallate, sodium bisulfite, sodium formaldehyde sulfoxylate, sodium metabisulfite, sodium sulfite, sodium thiosulfate and sulfur dioxide (see USP-NF).

The terms "preservative agent" as used herein are meant to refer to any ingredient capable of retarding or preventing microbial or chemical spoilage and protecting against discoloration. Without being so limited, they include benzalkonium chloride, benzethonium chloride, benzyl alcohol, butylparaben, chlorobutanol, chlorocresol, cresol, ethylparaben, methylparaben, myristyl gamma-picolinium chloride, phenol, phenoxyethanol, phenylmercuric acetate, phenylmercuric nitrate, propylparaben and thimerosal.

The terms "isotonic agent" as used herein are meant to refer to ingredients capable of adjusting osmolarity. Without being so limited, they include dibasic sodium phosphate, sodium bicarbonate, calcium chloride, potassium chloride, sodium lactate, glycerol, sorbitol, xylitol, sodium chloride, dextrose, a Ringer's solution, a lactated Ringer's solution and a mixture of dextrose and a mixture thereof (see relevant sections of USP-NF). A lactated Ringer's solution is a solution of recently boiled distilled water containing 39 mmol/L of sodium ion, 42 mmol/L of chloride ion, 0.6 mmol/L of bicarbonate ion, 1.4 mmol/L of potassium ion and 42 mmol/L of calcium ion—the same concentrations as their occurrence in body fluids. Ingredients are: NaCl 2.25 g, KCl 0.105 g, CaCl$_2$ 0.12 g, NaHCO$_3$ 0.05 g.

The term "solvent" as used herein is meant to refer to ingredients capable of facilitating the solubilization of an active ingredient within the formulation. Without being so limited, it includes water, water-alcohol solutions, emulsions or suspensions, including saline and buffered medical parenteral vehicles including sodium chloride solution, Ringer's dextrose solution, dextrose plus sodium chloride solution, Ringer's solution containing lactose and fixed oils. Intravenous vehicles may include fluid and nutrient replenishers, electrolyte replenishers such as those based upon Ringer's dextrose, and the like.

The term "stabilizer" as used herein is meant to refer to ingredients that enable a higher amount of active ingredients (e.g., radiosensitizer and/or anti-cancer agent) to be included in delivery system (e.g., liposomes), or that increase the pharmacokinetic of compositions of the present invention. For example, without being so limited, useful radiosensitizer compound (e.g., gold particles) stabilizers for the present invention include polyacrylamide, polyvinyl, dextrose, D-glucose and dithiolated diethylenetriaminepentaacetic acid (DTDTPA). These stabilizers reduce aggregation of the gold nanoparticles into larger particles. Such stabilizers may be used during production of nanoparticles.

Parenteral Formulations

In cases where parenteral administration is elected as the route of administration, pharmaceutical compositions of the present invention may be provided to patients in combination with additional pharmaceutically acceptable sterile aqueous or non-aqueous solvents, suspensions or emulsions. Formulations to be used for in vivo administration are preferably sterile. This is readily accomplished, for example, by filtration through sterile filtration membranes.

Pharmaceutically acceptable carriers for parenteral formulations include sterile aqueous solutions or dispersions and sterile powders for the extemporaneous preparation of sterile injectable solutions or dispersions. Aqueous solvents/carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, and fixed oils. Intravenous vehicles may include fluid and nutrient replenishers, electrolyte replenishers such as those based upon Ringer's dextrose, and the like.

Supplementary active ingredients such as additional anti-cancer agents or radiosensitizers can be incorporated into the compositions. "Pharmaceutically or pharmacologically acceptable" refer to compositions that do not produce an adverse, allergic or other untoward reaction when administered to an animal or a human, as appropriate.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

Route of Administration

The therapeutic compositions of the present invention can be administered in the form of injectable compositions (e.g., intravenously, intramuscularly, subcutaneously and intra-articularly), either as liquid solutions or suspensions; solid forms suitable for solution in, or suspension in, liquid prior to injection also may be prepared. These preparations also may be emulsified. Other pharmaceutically acceptable carriers include aqueous solutions, non-toxic excipients including salts, preservatives, buffers and the like.

Examples of non-aqueous solvents are propylene glycol, polyethylene glycol, vegetable oil and injectable organic esters such as ethyloleate. Intravenous vehicles include fluid and nutrient replenishers. Preservatives include antimicrobial agents, anti-oxidants, chelating agents and inert gases. The pH and exact concentration of the various components of the pharmaceutical composition are adjusted according to well-known parameters.

Pharmaceutical compositions can also be administered by routes such as orally, nasally, rectally, topically, intravenously, intramuscularly, subcutaneously, sublingually, intrathecally, intraperitoneally, intra-articularly or intradermally. Preferably, the route of administration is intravenously, intra-arterially or orally. Preferably, the pharmaceutical compositions are administered intravenously or intra-arterially.

Hence in specific embodiments, when the composition of the present invention is for oral administration, the composition is in a tablet, a solution or capsule such as a soft gel capsule for example. In other specific embodiments, when the composition of the present invention is for oral administration, it has an enteric coating. In other specific embodiments, when the composition of the present invention is for oral administration, it is an oil-based syrup.

Dosage

The compositions and formulations of the present invention are administered in amounts and at frequencies sufficient to treat cancer. A subject's progress can be determined by measuring and observing changes in the concentration of cancer markers; by measuring the actual size of the tumor over time and/or by determining any other relevant clinical markers which are well-known in the art. The determination, measurement, and evaluation of such characteristics and markers associated with clinical progress are known to those of ordinary skill in the art.

Any amount of a pharmaceutical composition can be administered to a subject. The dosages will depend on many factors including the mode of administration, the type of metal radiosensitizer and anti-cancer agent used and the age of the subject.

As used herein, the terms "effective amount" or "therapeutically effective amount" are meant to refer to an amount effective to achieve the desired therapeutic effect or biological effect while avoiding adverse side effects. Thus, an effective amount of a metal radiosensitizer of the present invention is an amount sufficient to provide a synergistic effect with an anti-cancer agent during irradiation. Similarly, an effective amount of an anti-cancer agent of the present invention is an amount sufficient to provide a synergistic effect with a metal radiosensitizer during irradiation. This synergistic effect is characterized by an increase in the number of strand breaks (double strand and/or single strand, preferably double strand breaks) of DNA in cells which are contacted with the radiosensitizer and anti-cancer agent and which are treated with radiation therapy. Typically and depending on the route of administration and anti-cancer agent, the compositions of the present invention comprise a ratio of metal radiosensitizer: anti-cancer agent that will allow for an increase in the number of DNA strand breaks in cancer cells as compared to combined radiation and chemotherapy, or to combined radiotherapy and metal radiosensitizer. Generally, the ratio between the radiosensitizer and anti-cancer agent is between 1:1 and 1:1000; more particularly between 1:1 and 1:500; between 1:1 and 1:200; between 1:1 and 1:100, 1:1 and 1:50; between 1:1 and 1:20, and between 1:2 and 1:20. Additional non-limiting examples of ratio that may be used in accordance with the present invention include a ratio of radiosensitizer:anti-cancer agent of 1:1, 2:1, 3:1, 4:1, 5:1, 6:1, 7:1, 8:1, 9:1, 10:1, 1:2, 1:3, 1:4, 1:5, 1:6, 1:7, 1:8, 1:9, 1:10.

An effective amount of the therapeutic composition is determined based on the intended goal. The term "unit dose" or "dosage" refers to physically discrete units suitable for use in a subject, each unit containing a predetermined quantity of the therapeutic composition calculated to produce the desired response, discussed above, in association with its administration, i.e., the appropriate route and treatment regimen. The quantity to be administered, both according to number of treatments and unit dose, depends on the desired effect.

Precise amounts of the therapeutic composition also depend on the judgment of the practitioner and are peculiar to each individual. Factors affecting dose include physical and clinical state of the patient, the route of administration and the potency, stability and toxicity of the particular radiosensitizer and anti-cancer agent.

Thus, the dosage will also be adapted by the clinician in accordance with conventional factors such as the extent of the disease (e.g., stage of the cancer, type of cancer, etc. . . . ), the particular anti-cancer agent used and different parameters from the patient (e.g., age, sex, general health, etc. . . . ) and may depend on whether the subject is also taking other drugs for treating another disease or condition. For example, preclinical studies with Lipoplatin™ and Lipoxal™ were conducted with 100 mg/m$^2$ to 350 mg/m$^2$ of anticancer agent. The body surface area (BSA) is the total surface area of the human body. The BSA is used in many measurements in medicine, including the calculation of drug dosages and the amount of fluids to be administered. The "normal" BSA is generally taken to be 1.7 m$^2$ but, in actual fact, the BSA depends on more than just height and weight. Other influential factors include the age and gender of the individual. For example, Average BSA for adult men: 1.9 m$^2$; Average BSA for adult women: 1.6 m$^2$; Average BSA for children (9 years): 1.07 m$^2$; Average BSA for children (10 years): 1.14 m$^2$; Average BSA for children (12-13 years): 1.33 m$^2$. The dosage is adapted accordingly.

Dosages may be provided in either a single or multiple dosage regimens. It could be administered, for example, every day for 3, 4, 5, 7, 8, 10 days or more. Alternatively, it may be administered once a week for 1, 2, 3, 4, 5, 6, 7, 8, 9 or 10 weeks or for as many weeks as the skilled practitioner sees fit. The radiosensitizer and anti-cancer agent can be administered separately or together and may be part of a single formulation or of separate formulations as long as they are administered prior to radiotherapy and that their biological concentration is in an effective amount in cells at the time of irradiation.

Liposomes

The degree of radiosensitization is directly related to the degree of metal radiosensitizer adduction. Hence, a prolonged infusion of the radiosensitizer in free form would maximize its incorporation. In addition, the total number of cells that must be sensitized to obtain any significant effect on the tumor is also important, as well as the rate of hepatic degradation and elimination. According to specific embodiments, the present invention, seeks to optimize the number of sensitized cells and to reduce hepatic degradation by encapsulating the anti-cancer agent and metal radiosensitizer in liposomes.

"Liposome" is a generic term encompassing a variety of single and multilamellar lipid vehicles formed by the generation of enclosed lipid bilayers.

Liposomes can be filled with drugs and used to deliver drugs for cancer and other diseases. Membranes are usually made of phospholipids, which are molecules that have a head and a tail. The head is attracted to water, and the tail, which is made of oil (hydrocarbon), is repelled by water. In nature, phospholipids are found in stable membranes composed of two layers (a bilayer). In the presence of water, the heads are attracted to water and line up to form a surface facing the water. The tails are repelled by water, and line up to form a surface away from the water. In a cell, one layer of heads faces outside of the cell, attracted to the water in the environment. Another layer of heads faces inside the cell, attracted by the water inside the cell. The hydrocarbon tails of one layer face the hydrocarbon tails of the other layer, and the combined structure forms a bilayer. When membrane phospholipids are disrupted, they can reassemble into tiny spheres/vesicles, smaller than a normal cell, either as bilayers or monolayers and these vesicles are called liposomes.

The lipids in the plasma membrane are chiefly phospholipids like phosphatidyl ethanolamine and cholesterol. Phospholipids are amphiphilic with the hydrocarbon tail of the molecule being hydrophobic and its polar head hydrophilic. As the plasma membrane faces watery solutions on both sides, its phospholipids accommodate this by forming a phospholipid bilayer with the hydrophobic tails facing each other. They can carry a net positive charge, a net negative charge or be neutral. For example, dicetyl phosphate can be employed to confer a negative charge on the liposomes, and stearylamine can be used to confer a positive charge on the liposomes.

Further advances in liposome research have been able to allow liposomes to avoid detection by the body's immune system, specifically, the cells of the reticuloendothelial system (RES). These liposomes are known as "stealth liposomes", and are constructed with Polyethylene Glycol (PEG)

studding the outside of the membrane. The PEG coating, which is inert in the body, allows for longer circulatory life (2-3 days) for the drug delivery mechanism.

Liposomes are used for drug delivery due to their unique properties. Dissolved hydrophilic solutes cannot readily pass through the lipids. Hydrophobic chemicals can be dissolved into the membrane, and in this way liposomes can carry both hydrophobic molecules and hydrophilic molecules. To deliver the molecules to sites of action, the lipid bilayer can fuse with other bilayers such as the cell membrane, thus delivering the liposome contents. By making liposomes in a solution of DNA or drugs (which would normally be unable to diffuse through the membrane), they can be (indiscriminately) delivered past the lipid bilayer.

Another interesting property of liposomes is their natural ability to target tumor tissues. The endothelial walls of all healthy human blood vessels are encapsulated by endothelial cells that are bound together by tight junctions. These tight junctions stop any large particles in the blood from leaking out of the vessel. Tumor vessels do not contain the same level of seal between cells and are diagnostically leaky. This ability is known as the Enhanced Permeability and Retention effect. Liposomes of certain sizes, typically less than 400 nm, can rapidly enter tumor sites from the blood, but are kept in the bloodstream by the endothelial wall in healthy tissue vasculature. Anti-cancer drugs such as Doxorubicin™ (Doxil), Camptothecin™, Daunorubicin™ (Daunoxome), Lipoplatin™ (cisplatin) and Lipoxal™ (oxaliplatin) are currently being marketed in liposome delivery systems.

Liposomes can also be designed to deliver drugs in other ways. Liposomes that contain low (or high) pH can be constructed such that dissolved aqueous drugs will be charged in solution (i.e., the pH is outside the drug's pI range). As the pH naturally neutralizes within the liposome (protons can pass through some membranes), the drug will also be neutralized, allowing it to freely pass through a membrane. These liposomes work to deliver drug by diffusion rather than by direct cell fusion. Another strategy for liposome drug delivery is to target endocytosis events. Liposomes can be made in a particular size range that makes them viable targets for natural macrophage phagocytosis. These liposomes may be digested while in the macrophage's phagosome, thus releasing its drug. Liposomes can also be decorated with opsonins and ligands to activate endocytosis in other cell types.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem (La Jolla, Calif.); DPPC and DPPC-Peg2000, DC-Chol, dimyristyl phosphatidylglycerol ("DMPG") and other lipids may be obtained from Avanti Polar Lipids, Inc. (Birmingham, Ala.). Stock solutions of lipids in chloroform, chloroform/methanol or t-butanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are often preferably not used as the primary phosphatide, i.e., constituting 50% or more of the total phosphatide composition, because of the instability and leakiness of the resulting liposomes.

Liposomes within the scope of the present invention can be prepared in accordance with known laboratory techniques. In one embodiment, liposomes can be prepared by mixing liposomal lipids in a solvent, in a container, e.g., a glass or pear-shaped flask. The container optimally has a volume ten times greater than the volume of the expected suspension of liposomes. Using a rotary evaporator, the solvent is removed at approximately 40° C. under negative pressure. The solvent normally is removed within about 5 min to 2 h, depending on the desired volume of the liposomes. The composition can be dried further in a desiccator under vacuum. The dried lipids generally are discarded after about 1 wk because of a tendency to deteriorate with time.

Dried lipids can be hydrated at approximately 25-50 mM phospholipid in sterile, pyrogen-free water by shaking until all the lipid film is resuspended. The aqueous liposomes can then be separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in Drug Carriers In Biology and Medicine, G. Gregoriadis (1979), the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

Preferred liposomes of the present invention are peggylated and of the type used in the Lipoplatin™ formulation. Because they have PEG coating, they enter in the category of stealth liposomes. This liposomal formulation allows for longer circulatory life (half life of 2-3 days). Because such liposomal formulations avoid detection by the body's immune system (specifically the cells of the reticuloendothelial system) and have a preferential accumulation to the tumor site, they have a less toxic effect on healthy tissues (19).

Where clinical application of liposomes containing radiosensitizer and anti-cancer agent is undertaken, it is desirable to prepare the liposome complex as a pharmaceutical composition appropriate for the intended application. Generally, this entails preparing a pharmaceutical composition that is essentially free of pyrogens, as well as any other impurities that could be harmful to humans or animals. One also will generally desire to employ appropriate buffers to render the complex stable and allow for uptake by target cells.

Thus, aqueous compositions of the present invention can comprise an effective amount of the radiosensitizer and anti-cancer agent in a liposome as discussed above, further dispersed in pharmaceutically acceptable carriers and/or aqueous media. Such compositions also are referred to as innocula.

The present invention is illustrated in further details by the following non-limiting examples.

Example 1

Material & Methods

Sample Preparation

Supercoiled plasmid DNA [pGEM-3Zf(−), 3197 base pairs], GNP and GNP-DNA and cisplatin-DNA complexes were prepared and purified as previously described (5, 6). The trace of TE buffer (Tris-HCl and EDTA) was removed by a Sephedex™ G-50 (Pharmacia) column. The pure DNA was diluted in distilled and deionized water (dd $H_2O$) without any salt. A solution of cis-diammineplatinum(II) dichloride (cisplatin, 98% purity, Sigma Aldrich) was mixed with the plasmid DNA solution to obtain a molar ratio (R) of cisplatin to plasmid molecules of 2:1. The mixture was kept in darkness at 37° C. for 48 h forming the DNA-cisplatin complex. In reacting with DNA, cisplatin loses its chloride ions and usually binds to the N7 position of guanine at a GG site, producing about 90% of an interstrand adduct (7). Thus, the cisplatin adduct to DNA carries a position charge (2+).

GNP were synthesized by mixing the 10 ml of 8 mM $NaBH_4$ with 10 ml of 3 mM $HAuCl_4$ (Sigma) (5). The average diameter of GNP was 5±2 nm (i.e., 3-7 nm), as characterized by TEM. Taking into account the size distribution and assuming a cubic close packing of the Au atoms (0.288 nm Dia.), the number of gold atoms per GNP and the concentration of the GNP solution were deduced to be 3000 and 0.5±0.2 μM, respectively (8).

The GNP-DNA and DNA-cisplatin-GNP complexes were prepared by mixing DNA or the DNA-cisplatin complex with the GNP solution so as to obtain the molecular ratios (1:2), (1:1) and (1:2:1), respectively. These ratios were chosen to remain close to those of clinical conditions relative to cisplatin concentration (Zheng Y, Sanche L. Gold nanoparticles enhance DNA damage induced by anti-cancer drugs and radiation. *Radiat Res.* 2009 July; 172(1):114-9) while providing an easily observable enhancement factor (EF), defined as the yield measured from a given complex divided by that obtained from pure DNA. With this preparation, the GNPs were electrostatically bound to DNA (5). Since the gold nanoparticles are slightly negatively charged (9), they are expected to be attracted to the positively charged site (i.e., counter ion of the phosphate group) within the DNA molecules. Furthermore, the induced polarization in DNA by the gold nanoparticle negative charge as well as the charge-dipole interaction add to the binding potential. When cisplatin is already bound to DNA, the positive charge on the cisplatin adduct should also contribute to this electrostatic interaction. In clinical use, it is not necessary that the metal be negatively charged to remain in proximity of DNA.

Electron Irradiation

Five μl aliquots of DNA, cisplatin-DNA, GNP-DNA and DNA-cisplatin-GNP solutions were deposited on a 1-mm-thick gold foil (99.99%, Laboratoire MAT). The samples were dried in a glove box at ambient temperature, at a relative humidity of 10%. This procedure produced films of 2900 nm average thickness estimated from the density of DNA of 1.7 g $cm^{-3}$ (10). Analysis of TEM images of GNP-DNA showed local binding of the GNP to DNA. Variations in the number of GNP present within small different areas of the sample (200× 200 $nm^2$) indicated that the sample thickness did not vary by more than 30%. Similar observations could be made with films of DNA-cisplatin-GNP complexes. It is estimated from these images that the film is sufficiently thick and uniform to absorb sufficient energy from the electron beam, while avoiding the effects of secondary electrons emitted from the metal substrate.

Afterwards, the samples were transferred to the TEM (H-7100 Hitachi) chamber, where they were irradiated or not by the 60 KeV electron beam with a current of 15 μA for periods varying from 5 to 30 s. Data were recorded at five different doses under identical experimental conditions and each data point was the average of three experiments. The incident electron fluence of the TEM was measured with a radiochromatic dosimetry film as described previously (11). Taking into account the area of the electron beam of 4.6 $mm^2$, the incident electron flux was determined to be $2.9 \times 10^{13}$ electrons $s^{-1}$ $cm^{-2}$. For the same fluence, the radiation dose absorbed by the GNP-DNA and DNA-cisplatin-GNP complexes was larger than that of pure DNA due to the larger mass absorption coefficient of gold and Pt.

Agarose Gel Electrophoresis

Once removed from the UHV chamber, the samples were recovered by dissolving in 20 μl of dd $H_2O$. The different forms of SSB, DSB and supercoiled DNA were separated by 1% neutral agarose gel electrophoresis (5, 6). The gels were scanned with a STORM860™ in the blue fluorescence mode (Molecular Dynamics) having an excitation wavelength of 450 nm. The relative amount of DNA in each form was quantified with the ImageQuant™ (Molecular Dynamics).

Example 2

Synergistic Effect of Metal Nanoparticles and Cisplatin in the Production of DSB and SSB on DNA Various complexes of DNA were prepared with different molar ratios (R) of adduct to DNA. Films of pure DNA and the complexes GNP-DNA (R=1:1 and 1:10), cisplatin-DNA (R=2:1) and cisplatin-GNP-DNA (R=2:1:1 and 20:1:10) were exposed to the 60 keV electron beam of a transmission electron microscope (TEM). After a given electron fluence, the samples were retrieved from the TEM and the DNA damage analyzed by electrophoresis. The dependence of the yields of single and double strand breaks (SSB and DSB) as well as the loss of supercoiled DNA were measured as functions of exposure. Since most radiation treatments use 1-18 MeV photons, which generate essentially Compton electrons over a wide energy range, the action of 60 KeV electrons is considered to represent the interaction of the high energy electrons liberated in cancer cells during radiotherapy (4).

The curves in FIG. 1 show the dependence of the yields of DSB on exposure to 60 keV electrons of films of pure plasmid DNA and the complexes of cisplatin-plasmid, GNP-plasmid and cisplatin-GNP-plasmid for R=2:1, 1:1, and 2:1:1, respectively. Similar curves were generated for SSB (data not shown). If the current density of electrons impinging on the target is defined as J, an infinitesimal relative number of damaged products can be expressed as:

$$dN/N = \sigma J dt,$$

where N is the number of DNA molecules in the sample, σ the cross section corresponding to the total DNA damage. Integration over time gives $$N_s(t) = N_s(o) \exp(-\sigma J t),$$

where $N_s(o)$ and $N_s$ are the initial and the final amount of supercoiled DNA molecules in the sample, respectively. If this exponential function is expanded into the Taylor's series around a small time interval and the first two terms of the expansion are kept, the equation giving the decrease of supercoiled DNA becomes $$N_s(t) = N_{so}(1 - \sigma J t).$$

and the total damage $N_d(t) = N_s(o) - N_s(t) - N_s(o) \sigma J t$.

Defining $N_{ss}$, $N_{ds}$ and $N_r$ as the damage and $\sigma_u$, $\sigma_{ds}$ and $\sigma_r$ as the cross sections for damage in the form of SSB, DSB and the remaining lesions, respectively, due to SSB, DSB and the remaining of the lesions, respectively, it can be written that $$N_d(t) = N_{ss}(t) + N_{ds}(t) + N_r(t) = N_s(o) J t [\sigma_{ss} + \sigma_u + \sigma_r]$$

It follows that individual damages to DNA can be expressed as the initial slope of an exponential function. The curves drawn through the data points in FIG. 1 were therefore fitted to an exponential function. The yields of supercoiled DNA, SSB and DSB per electron per molecule, expressed as the percentage of initial DNA in the film, were obtained from the initial slope of such exponential fits. The results at zero fluence, obtained under identical conditions, indicate that the complexes were more fragile than pure DNA to the manipulations. Since they were recorded from the linear portion of the dose-response curves, these yields were generated by the interaction of a single 60 keV electron. They are given in Table 1 below for different DNA film preparations. Both GNP and cisplatin binding to DNA increase the production of SSB and DSB, but the highest yields were obtained with both species bound to DNA.

TABLE 1

The yields (Y in $10^{-15}$ electron$^{-1}$ molecule$^{-1}$) for the formation of SSB, DSB and loss of supercoiled DNA induced by 60 keV electrons in 2900 nm thick films of DNA of different compositions deposited on a gold foil. The quoted errors represent the maximum deviations of three identical measurements.

| | Y | | |
|---|---|---|---|
| Samples | SSB | DSB | Loss of Supercoiled |
| pure DNA | 3.72 ± 0.3 | 0.77 ± 0.1 | −5.46 ± 0.54 |
| GNP:DNA = 1:1 | 8.65 ± 0.9 | 1.79 ± 0.2 | −10.5 ± 1.1 |
| Cisplatin:DNA = 2:1 | 9.49 ± 0.91 | 1.95 ± 0.2 | −12.3 ± 1.2 |
| Cisplatin:GNP:DNA = 2:1:1 | 11.1 ± 1.2 | 7.68 ± 1.0 | −20.1 ± 2.0 |
| GNP:DNA = 1:10 | 5.38 ± 0.56 | 1.11 ± 0.3 | −6.8 ± 1.0 |
| Cisplatin:GNP:DNA = 20:1:10 | 10.2 ± 1.1 | 3.93 ± 0.5 | −14.9 ± 1.6 |

Figure 2:
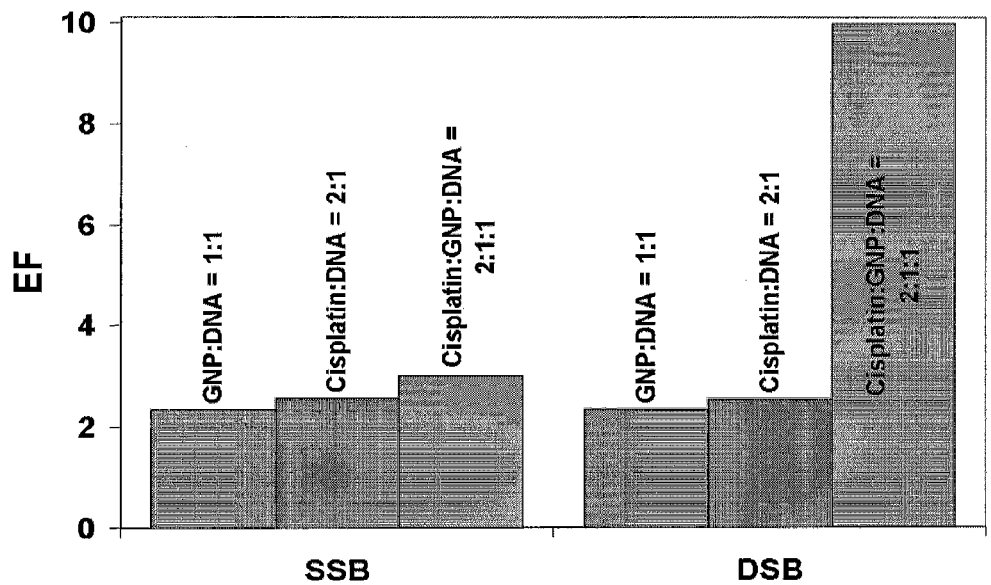
FIG. 2 shows the enhancement factor (EF) relative to pure DNA of GNP-DNA (1:1), cisplatin-DNA (2:1) and cisplatin-GNP-DNA (2:1:1) complexes for SSB and DSB induced by 60 keV electrons.
Figure 3:
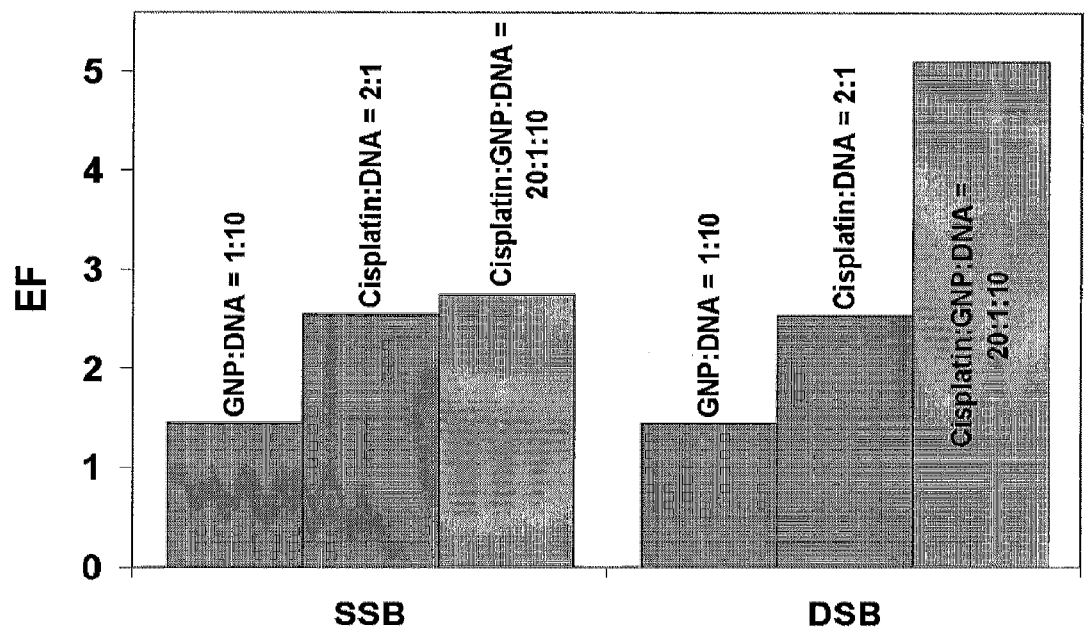
FIG. 3 shows the enhancement factor (EF) relative to pure DNA of GNP-DNA (1:10), cisplatin-DNA (2:1) and cisplatin-GNP-DNA (20:1:10) complexes for SSB and DSB induced by 60 keV electrons.

The histograms of FIGS. 2 and 3 exhibit the EF defined previously. For ratios of GNP to DNA of 1:1 and cisplatin to DNA of 2:1, the EF of SSB lies between 2-2.5 and increases to 3 with cisplatin-GNP-plasmid in a ratio of 2:1:1. A similar effect is observed for DSB with the exception that the binding of GNP and cisplatin to DNA creates a spectacular increase in the EF; i.e., DSB are increased by an order of magnitude with respect to pure DNA. As shown in FIG. 3, even when the GNP-DNA ratio is lowered to 1:10, the EF for DSB is still as high as 5.1.

When only one GNP was added to a cisplatin-DNA complex before irradiation by high energy electrons, the production of DSB was increased by a factor of 4. Even when only one GNP was electrostatically bound to one cisplatin-DNA complex out of 10, the yield of DSB from the cisplatin-DNA complex was doubled. Compared to the yield of DSB from pure DNA, these enhancements translate into EFs of 9.9 and 5.1, respectively. Since the number of generated additional LEE is directly proportional to the number of GNP, this non-linearity between the number of GNP and the EF was surprising. Such a high sensitivity of cisplatin-DNA complexes to irradiated GNP cannot be explained by any changes that may be induced in DNA by the GNP, since in this case the additional damage would be directly proportional to the number of GNP up to R of 1:1. As shown in previous experiments on DNA damage induced by 60 keV radiation incident 300 nm films of GNP-DNA complexes, the formation of DSB as a function of the ratio GNP/plasmid rose rapidly between 0 and 0.25 and tended to saturate thereafter. The previous results and present EF values point to damage caused by the generation of additional secondary electrons from the GNP, which can reach many DNA molecules. Since the diameter of the DNA is 2 nm, secondary electrons of energy lower than 200 eV, which have an effective range of about 10 nm (15, 16), could reach 10 DNA molecules in the films. For 60 keV electrons, gold has a mass absorption coefficient approximately 9 times larger than that of biological material (17). Additional ions and secondary electrons are generated by about the same factor in this metal; the latter can easily escape the GNP and further damage nearby DNA. The most probable energy of secondary electrons usually lies around 9-10 eV, with most secondary electrons having energies well below 200 eV (18). Thus, the local density of LEE near DNA was greatly increased and, as seen from FIGS. 2 and 3, the presence of one GNP per plasmid about doubled the formation of SSB and DSB.

When both cisplatin and GNP were bound to DNA, the EF for SSB increased about threefold. A strong synergy is observed between GNP and cisplatin in the case of DSBs, which are increased by an order of magnitude for R=2:1:1 (FIG. 2). A number of basic phenomena could contribute to this huge enhancement. First, the possibility of two-event processes triggered by the interaction of a single 60 keV electron with a GNP can be considered. The yield of DSB is expected to be highly dependent on two-event processes, such as the damage created by two LEE within the range of the distance between 10 base pairs (~4 nm). Furthermore, a SSB/DSB ratio of 4-5 has been observed in several LEE irradiation experiments compared to that of 10-20 for photons. As previously mentioned, GNPs increase the density of LEE within 10 nm of their site by an average factor of about 9 in the case of 60 keV radiation. Hence, DSB formation by two LEE interactions is expected to considerably increase within the distance of 10 base pairs from a GNP. Following DEA, simultaneous electron transfer and reaction of $NH_3$ or the Pt(I) adduct could also cause a DSB. The much higher EF obtained by combining cisplatin and GNP compared to GNP alone may also partly arise from the energy requirement to produce a DSB. Cisplatin locally modifies the topology of DNA (7). The different topology could potentiate DNA damage and raise the amount of DSB produced with and without irradiation. Combined with the electron affinity and chemical reactivity of cisplatin, these modifications could appreciably lower the energy required to break two adjacent bonds. The energy required to break bonds being lower, the probability of breaking bonds will be higher which leads to a better efficiency and a better control of tumoral proliferation.

It has been shown that the binding of only one GNP to a plasmid-cisplatin complex containing 3197 base pairs increased by a factor of 4 the efficiency of the chemotherapeutic agent cisplatin to produce DSB in DNA irradiated by high energy electrons. Furthermore, the overall increase in DSB compared to pure DNA reached an order of magnitude. The present results were obtained with $6.25 \times 10^{-4}$ cisplatin molecules per base pair (mol./b.p.). In chemotherapy, with cisplatin incorporated into a liposome, concentrations can reach values of $4 \times 10^{-4}$ cisplatin mol./b.p. in DNA, assuming a uniform distribution of the drug in cancer tissues (19). Since cisplatin accumulates preferentially in the DNA of cancer cells (20), the present work should therefore easily represent clinical concentrations.

Example 3

Liposomes Encapsulated Gold Nanoparticles and Platinum Anti-Cancer Agent

Composition of LipoGold™

Lipids composition in molar ratio: Dipalmitoylphosphatidylcholine (DPPC)=1.3:3β-[N—(N',N'-dimethylaminoethane)-carbamoyl]-cholesterol (DC-Chol)=1:Dioleoyl Phosphatidylethanolamine (DOPE)=1:DPPC-Peg$_{2000}$=0.033.

Load: Gold nanoparticles (AuNp) solution: size of gold=5.6 nm, concentration=5 mM Cisplatin in a concentration of 5 mM.

Fabrication

Lipid Layer:

Lipids were thawed at room temperature and then mixed together at 52° C. in chloroform. Chloroform was removed using rotary evaporation (1 h, 52° C., 250 mbar, 120 rpm). After evaporation of the chloroform, a thin layer of lipids remained on the inner surface of the round bottom flask.

Hydration:

The load (AuNp+cisplatin) was diluted 1/30 in a solution of sterile clinical dextrose (Dextrose 5%). 1.5 ml of this solution was then used for hydration of the lipids bilayer with vigorous agitation.

Freeze and Thaw:

The solution of lipids and AuNp+cisplatin was subjected to 5 freeze-&-thaw cycles (5 min in liquid nitrogen, 5 min at 52° C./cycle).

Purification:

The liposomes resulting from the freeze-&-thaw step was diluted (1/2) and purified through a column of Sephadex™ G-25M and collected in three fractions. The purification step was performed to separate the liposomal formulation from the non encapsulated free AuNp and cisplatin. Fraction 1 was defined as a mix of solvent and liposomes of big size, Fraction 2 was a liposomal fraction used for the in vivo experiment in Example 4 below and Fraction 3 consisted of free AuNp and free cisplatin.

Analysis

Figure 4:
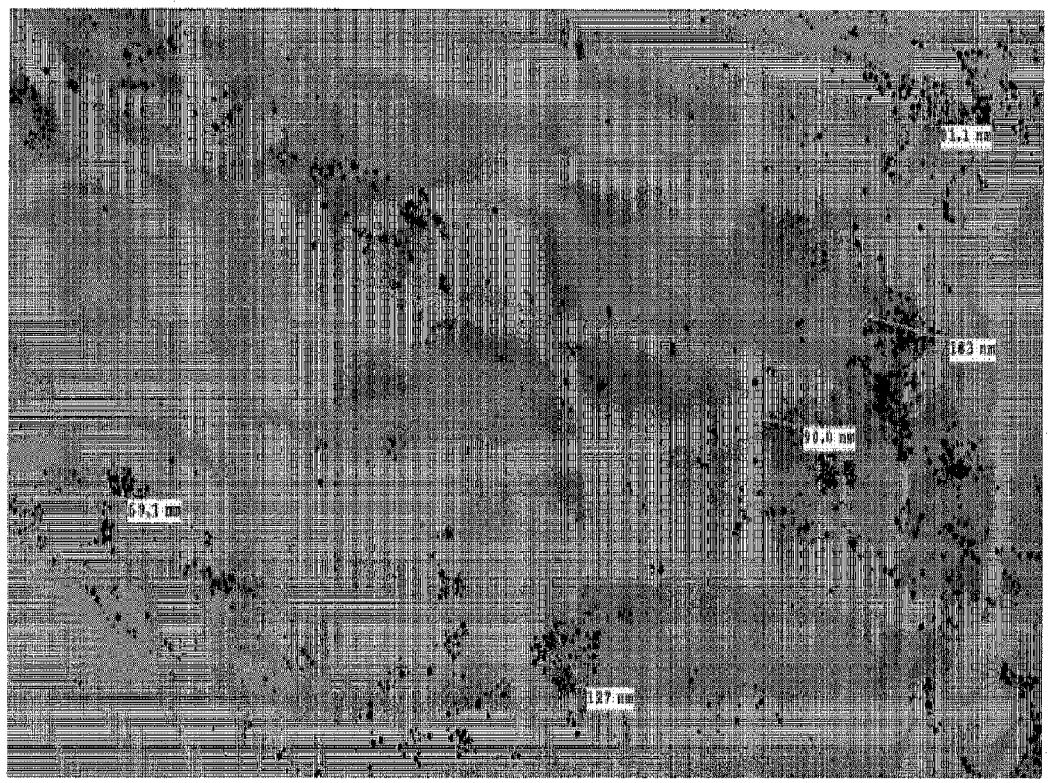
FIG. 4 shows the transmission electron microscopy (TEM) of GNP and platinum-compound-loaded liposomes of the fraction 1 of liposomes eluted in the Sephadex™ column described in Example 3.
Figure 5:
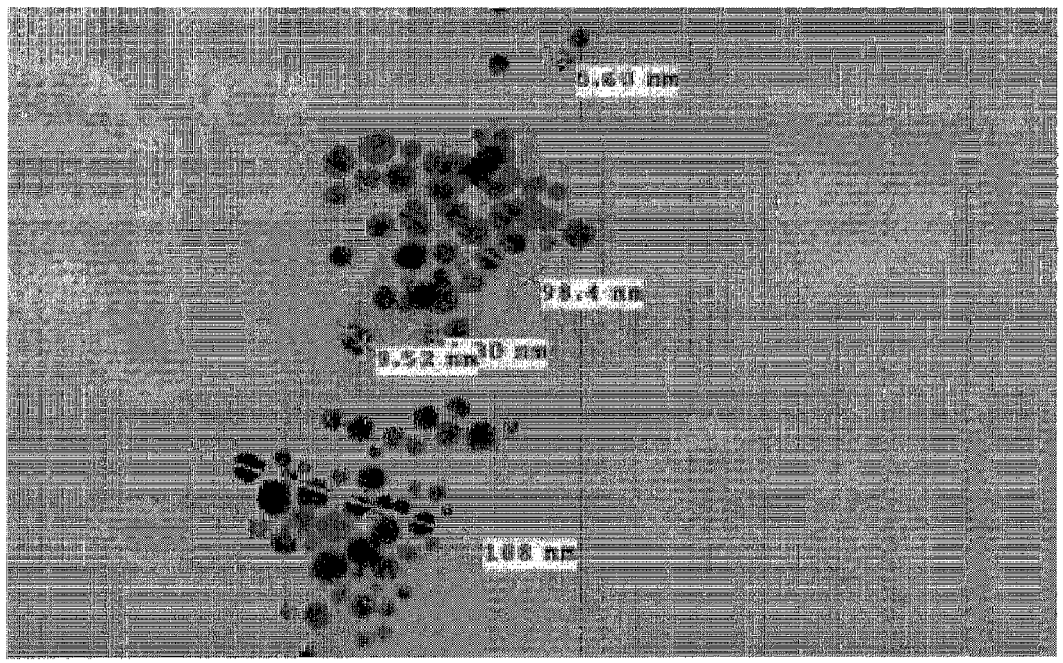
FIG. 5 shows the transmission electron microscopy (TEM) of GNP and platinum-compound-loaded liposomes of the fraction 2 of liposomes eluted in the Sephadex™ column described in Examples 3 and 4.

TEM (Transmission Electron Microscopy):

TEM images were taken for Fractions 1 and 2. As shown in FIGS. 4 (Fraction 1) and 5 (Fraction 2), there was an artefact of dispersion probably caused by the step of drying of the sample before image acquisition. The dispersion follows a drying pattern of agglutination probably caused by the viscosity of the solvent (dextrose 5%) that produced compaction and deformation of the liposomes when drying. Nevertheless, the TEM images allowed the observation of individual AuNp nanospheres with a mean diameter of 6 nm and the aggregation of these AuNp with a diameter of approximately 112.55 nm±40 nm (fraction 2). The lipid membrane of the liposomes is not visible because no staining agent (molybdene) was used for these TEM observations. Nevertheless, the characteristic agglomerations of AuNp suggests that AuNp particles (and cisplatin) were well entrapped into liposomes.

Concentration:

The concentration of Au and Pt of the liposomal formulation for Fractions 1 and 2 was measured by ICP-MS (Inductively coupled plasma mass spectrometer). Using standards as reference, the concentration of metal was as follows: Fraction 1: Au=0.875 µg/ml, Pt=0.885 µg/ml. Encapsulation efficiency=Au 52%, Pt 53%. Fraction 2: Au=2.89 µg/ml, Pt=2.4 µg/ml Encapsulation efficiency=Au 173%, Pt 143%. Ratio Au:Cisplatin of about 1:1.

The high encapsulation efficiency of Fraction 2 is likely due to a concentration of metal at the hydration step.

Example 4

In Vivo Administration of Liposomes-Encapsulated Gold Nanoparticles and Platinum Anti-Cancer Agent Fischer Rats The experimental protocol was approved by the institutional ethical committee and conformed to regulations of the Canadian Council on Animal Care. For all procedures (implantation, chemotherapy, radiotherapy and euthanasia), male Fischer rats (Charles River Laboratories) were anesthetised with an intraperitoneal injection of Ketamin/Xylazin (87/13 mg/ml) at 1 ml/kg and additional injection were delivered to maintain anaesthesia throughout the procedures when needed. When anesthetised, ocular lubricant was applied on the animal's eyes to avoid drying.

F98 Glial Cell Implantation in Fischer Rats Brain

F98 glioma tumors were implanted in Fischer rat brains as described by Blanchard et al. (Blanchard J, Mathieu D, Patenaude Y, Fortin D., MR-pathological comparison in F98-Fischer glioma model using a human gantry. Can J Neurol Sci. 2006 February; 33(1):86-91). Briefly, a midline scalp incision was performed on anesthetized animals to expose the bregma, and then the animal head was fixed on a stereotactic frame (David Kopf Instrument). A burr hole was drilled 3 mm to the right and 1 mm anterior to the bregma with a 16 s-gauge needle. A 25 s-gauge needle was inserted to a depth of 6.5 mm and then withdrawn to a target depth of 6 mm from the skull interior surface. The 25s-gauge needle (SGE) was held in a microinfusion pump (WPI model UMP3) fixed on the stereotactic frame. The pump driving unit (WPI model MICRO4 UMC4) was programmed to inject 1 µl/min on 5 min. for a total of 5 µl (10 000 cells) in the target location (the right frontal lobe). Two minutes after F98 glioma cells implantation, the syringe was slowly retracted over one minute, the burr hole was filled with bone wax and the scalp was closed by sutures. Antibiotic and analgesic ointment was then apposed on the sutures.

Intra Carotid Chemotherapeutic Drug Delivery

Ten days after F98 glioma cells implantation, LipoGold™ (Fraction 2) was infused in the internal carotid artery in a retrograde manner via the right external carotid as described by Fortin et al. (Fortin D, Adams R, Gallez A. A blood-brain barrier disruption model eliminating the hemodynamic effect of ketamine. Can J Neurol Sci. 2004 May; 31(2):248-53.).

After complete injection, the external carotid was sacrificed and the neck of the animal was closed by sutures. Antibiotic and analgesic ointment was then apposed on the sutures. The efficiency of LipoGold™ was compared to other platinum compounds using the same surgical procedures. To be able to administer a platinum compound dose that corresponds to a dose equivalent to that for human treatment, the first approximation of equivalent dose was established with respect to the body surface area (BSA), that is determined to be 0.04 $m^2$ for rats weighting 250 g. Platinum doses administered to rats in this study were 1 ml/rat of oxaliplatin 3 mg/ml, cisplatin 3 mg/ml, Lipoplatin™ 3 mg/ml (of cisplatin), Lipoxal™ 3 mg/ml (of oxaliplatin) and LipoGold™ 0.00289 mg/ml. Free platinum compounds were diluted in 1 ml of 5% dextrose solution (Baxter, Toronto, Canada). Lipoplatin™ and Lipoxal™ were used without dilution at a concentration of 3 mg platinum/ml. and the solutions of 1 ml of platinum formulation were injected over 20 min.

Sham Animals

Control animals had the same surgical procedures as animal treated with platinum drugs. These animals were implanted with F98 glioma cell line. Ten days after implantation, these animals received an intra-arterial injection of 1 ml of clinical dextrose 5% (solvent for platinum-based drugs) using the same procedures as other animals treated by platinum-based drugs.

Gamma Knife Irradiation

Twenty four hours after chemotherapeutic treatments (platinum-based drugs and sham), rats were anesthetized and positioned in home-made stereotactic frame for use with the Gamma Knife™ 4C (ELEKTA) (Charest G, Mathieu D, Lepage M, Fortin D, Paquette B, Sanche L. Polymer gel in rat skull to assess the accuracy of a new rat stereotactic device for use with the Gamma Knife. *Acta Neurochir (Wien)* 2009 June; 151(6):677-83; Epub 2009 Apr. 18). This stereotactic frame allows reliable positioning to target precisely the tumor volume including a minimum surrounding brain parenchyma volume. The 8-mm collimator was used to deliver radiation at predetermined coordinates targeting the tumor location. The tumor, that has roughly a diameter of 4 mm (Blanchard J, Mathieu D, Patenaude Y, Fortin D., MR-pathological comparison in F98-Fischer glioma model using a human gantry. *Can J Neurol Sci.* 2006 February; 33(1):86-91) and the surrounding brain volume were treated with a maximum dose of 15 Gy at a dose rate of approximately 2.8 Gy/min. For rats that received LipoGold™, radiation treatments were given 8 h after chemotherapy. For one rat, radiation was given in one shot of 15 Gy and two other rats, radiation was given in two shots of 7.5 Gy separated by 20 min.

End Point Experiment for Surviving Time

Weight, mobility, coordination, loss of self grooming (periocular secretion accumulation) and landing ability were evaluated daily. In accordance with the ethical committee regulations, the survival time end point of the experiment was complete lethargy (and apathy) of the animals. At this point, animals were anesthetised and an intracardiac infusion of paraformaldehyde 4% (PFA) was use to fix the brain tissue. The brain was removed by craniotomy to corroborate the presence of tumor and kept in PFA for future analysis.

Results of Surviving Assay

As was also observed for Lipoplatin™ and Lipoxal™, LipoGold™ did not produce any apparent toxicity on the animal treated following drug administration. Conversely, free cisplatin produced an apparent high toxicity. Animals that received cisplatin showed complete apathy shortly after the administration and died before sham animals. In the same manner, animals treated with oxaliplatin showed apparent high toxicity (parastesy, parasteny, lack of capillary blood flow, jump reflex and apathy) and had a short life span, similar to sham animals. Life spans for treated animals are shown in FIG. 6.

Conclusion

Figure 6:
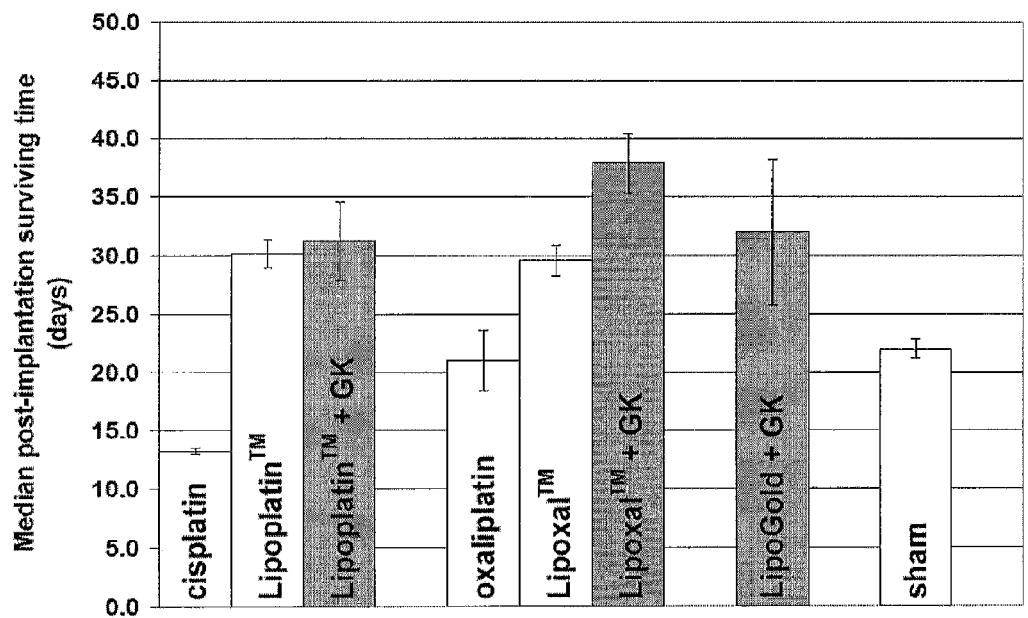
FIG. 6 presents the median surviving time obtained for seven animal groups. The number of animal for each group is: cisplatin=4, sham=6, Lipoplatin™=8, Lipoxal™=12, Lipoplatin™+GK=11, Lipoxal™+GK=9, LipoGold=3.
*GK=combination with Gamma Knife (i.e. radiation).

Even if the concentration of cisplatin in LipoGold™ is 1000 time less than the cisplatin concentration of Lipoplatin™ (i.e. 0.0024 mg/ml LipoGold™ vs. 3 mg/ml), the effect on the life span is about the same in both cases (FIG. 6). Furthermore, LipoGold™ did not produce apparent toxicity in healthy tissue.

Example 5

Determining the Synergistic Effect of the Combination of LipoGold™ and Radiation The synergistic effect of the combination of LipoGold™ and radiation will be further evaluated by combining different doses of LipoGold™ (e.g., 1 µM à 80 µM) alone or combined with radiation (Charest G, Paquette B, Fortin D, Mathieu D, Sanche L. Concomitant treatment of F98 glioma cells with new liposomal platinum compounds and ionizing radiation. *J Neurooncol.* 2010 April; 97(2):187-93. Epub 2009 Sep. 17). The survival fraction of each modality will be analysed for Combination Index (CI). These tests will determine an optimized ratio of AuNp and cisplatin in liposomes to achieve the best radiosensitizer effect. Briefly, the CI is calculated using the equation:

$$CI = \frac{(Pt)}{(Ptx)} + \frac{(IR)}{(IRx)} + \frac{(Pt)(IR)}{(Ptx)(IRx)}$$

where the denominator, (Ptx) is the concentration of platinum compound that inhibits colonies formation at x %, and (IRx) corresponds to the radiation dose which results in the same x % of colonies formation inhibition. In the numerator (Pt)(IR) "in combination" also inhibit the colonies formation at the equivalent x %. If the sum of these two fractions is equal to 1, additive effect is indicated. If the CI value is smaller than 1, synergism in indicated, and if the CI value is greater than 1, antagonism is suggested.

Example 6

Higher Doses of Platinum-Based Compound and Gold in LipoGold™

Non toxic AuNp stabilisers (polyacrylamide, polyvinyl, dextrose, D-glucose, dithiolated diethylenetriaminepentaacetic acid (DTDTPA)) are mixed with AuNp and cisplatin. The solution of stabilized AuNp and cisplatin (0.03 mg/ml, 0.3 mg/ml, 3 mg/ml, 4 mg/ml, 5 mg/ml, 6 mg/ml, 7 mg/ml, 8 mg/ml, 9 mg/ml) is encapsulated into liposomes.

Example 7

Determination of Maximum Tolerated Dose and Dose Limited Toxicity

The maximum tolerated dose (MTD) and dose limited toxicity (DLT) will be determined by classical in vivo pharmacologic assays. The role of toxicology studies in new anticancer drug development is essentially threefold: to define a safe starting dose for phase I clinical trials by determining the maximal tolerated dose (MTD) in animals; to catalogue the dose-limiting toxicity (DLT) and other toxicities to alert clinical investigators to potential problems in clinical studies; and to retract an agent from further evaluation due to excessive and unpredictable toxicity. Toxicology studies will be perform following the recommendation of the FDA (DeGeorge J J, Ahn C H, Andrews P A, Brower M E, Giorgio D W, Goheer M A, Lee-Ham D Y, McGuinn W D, Schmidt W, Sun C J, Tripathi S C. Regulatory considerations for preclinical development of anticancer drugs. *Cancer Chemother Pharmacol.* 1998; 41(3):173-85).

Example 8

Determination of Long-Term Stability

Leakage tests will be performed at different times after production of LipoGold™. At various times after manufacture, LipoGold™ solution samples will be deposited in osmotic bag shaving pores of 10 µM. This will enable the separation of intact liposomes from those which will have released their content i.e. the content will have crossed through the osmotic bag membrane. The fractions outside the bag and inside the bag will then be analyzed for their content in platinum compounds and radiosensitizer (e.g., gold nanoparticles). Exclusion columns can be used as an alternative to osmotic bags.

Example 9

Determination of Drug Tumor Uptake

Liposomes preferentially target tumors by means of the Enhanced Permeability and Retention (EPR) property of the neovascularisation of the tumor. Different lipid compositions (i.e. pH sensitive lipids, cationic lipids) will be used in the liposomes to increase the drug uptake by the tumor. The drug uptake will be measured in the tumor, adjacent healthy tissues, different organs such as kidney, liver and blood for each LipoGold™ formulation.

Although the present invention has been described hereinabove by way of specific embodiments thereof, it can be modified, without departing from the spirit and nature of the subject invention as defined in the appended claims.

REFERENCES

1. P. J. Eifel, Concurrent chemotherapy and radiation therapy as the standard of care for cervical cancer. *Nat. Clin. Pract Oncol.* 5, 248-255 (2006).
2. *Cancer: Principles and Practice of Oncology*, edited by V. T. Devita, S. Hellman and S. A. Rosenburg, 6th ed. Lippincott Williams and Wilkins, Philadelphia, Pa., 2001.
3. V. Brabec, *Platinum-based Drugs in cancer therapy*, edited by L R. Kelland and N. Farrell, Humana Press Inc., Totowa, N.J., 2000.
4. H. E. Johns and J. R. Cunningham, *The physics of Radiology*, edited by H. Springfield, Charles C. Thomas Publisher, U.S.A. 1983.
5. Y. Zheng, D. Hunting, P. Ayotte and L. Sanche, Radiosensitization of DNA by gold nanoparticles irradiated with high-energy electrons. *Radiat Res.* 169, 19-27 (2008).
6. Y. Zheng, D. Hunting, P. Ayotte and L. Sanche, Role of secondary low energy electrons in the concomitant chemoradiation therapy of cancer. *Phys. Rev. Lett.* 100, 198101-4 (2008).
7. R. N. Bose, Biomolecular targets for platinum antitumor drugs. *Mini-Rev. Med. Chem.* 2, 103-111 (2002).
8. M. J. Hostetler, J. E. Wingate, C. Zhong, J. E. Harris, R. W. Vache, M. R. Clark, D. Londono, S. J. Green, J. Stokes and R. W. Murray, Alkanethiolate gold cluster molecules with core diameter from 1.5 to 5.2 nm: core and monolayer properties as a function of core size. *Langmuir* 14, 17-30 (1998).
9. M. A. Hayat, Colloid Gold, Principles, Methods and Applications. Academic Press, New York, 1989.
10. G. D. Fashman, *Handbook of Biochemistry and Molecular Biology* $3^{rd}$ ed. CRC Press, Boca Raton, Fla., 1995.
11. Z. Cai, X. Pan, D. Hunting, P. Cloutier, R. Lemay and L. Sanche, Dosimetry of ultrasoft X-rays (1.56 keV $Al_{K\alpha}$) using radiochromatic films and color scanners. *Phys. Med. Biol.* 48, 4111-4124 (2003).
12. J. Berdys, I. Anusiewicz, P. Skurski and J. Simons, Damage to model DNA fragments from very low-energy (1<eV) electrons. *J. Am. Chem. Soc.* 126, 6441-6447 (2004).
13. Kumar and M. D. Sevilla, The role of $\pi\sigma^*$ excited states in electron-induced DNA strand break formation: A time-dependent density functional theory study. *J. Am. Chem. Soc.* 130, 2130-2131 (2008).
14. L. Sanche in "Radiation Induced Molecular Phenomena in Nucleic Acid, A comprehensive theoretical and experimental analysis series", Vol. 5, edited by M. K. Shukla and J. Leszczynski, Springer, Netherland, 2008.
15. J. Meesungnoen, J.-P. Jay-Gerin, A. Filali-Mouhim and S. Mankhetkorn, Low-energy electron penetration range in liquid water. *Radiat. Res.* 158, 657-660 (2002).
16. B. Boudaïffa, P. Cloutier, D. Hunting, M. A. Huels and L. Sanche, Cross sections for low-energy (10-50 eV) electron damage to DNA. *Radiat. Res.*, 157, 227-234 (2002).
17. Stopping power and range tables for electrons, Data from NIST website: http://physics.nist.gov/PhysRefData/Star/Text/ESTAR.html
18. S. M. Pimblott and J. A. LaVerne, Production of low-energy electrons by ionizing radiation. *Rad. Phys. Chem.* 76, 1244-1249 (2007).
19. T. Boulikas, Molecular mechanisms of cisplatin and its liposomally encapsulated form, Lipoplatin™, as a chemotherapy and antiangiogenesis drug. *Cancer Therapy* 5, 349-376 (2007).
20. N. Kitada, K. Takara, T. Minegaki, C. Itoh, M. Tsujimoto, T. Sakaeda and T. Yokoyama, Factors affecting sensitivity to antitumor platinum derivatives of human colorectal tumor cell lines. *Cancer Chemother. Pharmacol.* 62, 577-584 (2008).
21. Merrill S. Kies, Charles L. Bennett and Everett E. Vokes, Locally advanced head and neck cancer, Current Treatment Options in Oncology, vol. 2, No. 1, pp: 7-13.
22. Charest G. et al., Acta Neurochir. 2009 *Acta Neurochir (Wien)* 2009 June; 151(6):677-83.

The invention claimed is:

1. A method of potentiating ionizing radiotherapy which produces low energy electrons comprising:
    (a) administering to a subject in need thereof an effective amount of a composition comprising (i) an anti-cancer agent comprising platinum which binds to DNA and (ii) gold nanoparticles consisting of gold, and optionally, a stabilizer; and
    (b) administering to the subject ionizing radiotherapy which produces low energy electrons,
    wherein (a) occurs prior to (b); and
    whereby (a) potentiates the ionizing radiotherapy of (b).
2. A method of enhancing ionizing radiosensitivity of a cell population to ionizing radiation which produces low energy electrons, comprising:
    (a) exposing the cell population to an effective amount of a composition comprising (i) gold nanoparticles consisting of gold and optionally, a stabilizer and (ii) an anti-cancer agent comprising platinum and which binds to DNA; and
    (b) exposing the cell population to the ionizing radiation which produces low energy electrons,
    whereby (a) enhances the radiosensitivity of the cell population to the ionizing radiation of (b).
3. A method of increasing the amount of strand breaks in DNA in a cell exposed to ionizing radiotherapy which produces low energy electrons comprising:
    (a) contacting the cell with an effective amount of (i) an anti-cancer agent comprising platinum which binds DNA and (ii) gold nanoparticles consisting of gold and optionally, a stabilizer; and
    (b) submitting the cell to the ionizing radiotherapy which produces low energy electrons,
    whereby the method results in increasing the amount of DNA strand breaks as compared to a method of applying the ionizing radiotherapy alone.
4. The method of claim 3, wherein said anti-cancer agent comprising platinum is selected from the group consisting of cisplatin, carboplatin, oxaliplatin, and combinations thereof.
5. The method of claim 4, wherein said anti-cancer agent comprising platinum is cisplatin.
6. The method of claim 3, wherein said gold nanoparticles have an average diameter of between 1 and 60 nanometers.
7. The method of claim 3, wherein said strand breaks are double strand breaks.
8. The method of claim 3, wherein said anti-cancer agent and said gold nanoparticles are administered simultaneously.

9. The method of claim 3, wherein said anti-cancer agent and said gold nanoparticles are administered separately.

10. The method of claim 8, wherein said anti-cancer agent and said gold nanoparticles are encapsulated in liposomes.

11. The method of claim 10, wherein a majority of said liposomes have a diameter of less than 400 nm.

12. The method of claim 10, wherein a majority of said liposomes have a diameter between about 100 and about 150 nm.

13. The method of claim 12, wherein said liposomes are coated with polyethylene glycol (PEG).

14. The method of claim 10, wherein said liposomes preferentially target cancer cells.

15. The method of claim 14, wherein said liposomes comprise dipalmitoyl phosphatidyl glycerol (DPPG), soy phosphatidyl choline, cholesterol and methoxy-polyethylene glycol-distearoyl phosphatidyl-ethanolamine (mPEG$_{2000}$-DSPE).

16. The method of claim 14, wherein said liposomes comprise dipalmitoylphosphatidylcholine (DPPC), 3β-[N—(N', N'-dimethylaminoethane)-carbamoyl]-cholesterol (DC-Chol), Dioleoyl Phosphatidylethanolamine (DOPE) and polyethylene glycol (PEG).

17. The method of claim 15, wherein said liposomes have a mean diameter of between about 70 nm to 152 nm.

18. The method of claim 10, wherein the liposomes further comprise a stabilizer.

19. The method of claim 18, wherein the stabilizer is polyacrylamide, dextrose, D-glucose or dithiolated diethylenetriaminepentaacetic acid (DTDTPA).

20. The method of claim 3, wherein said gold nanoparticles have an average diameter of between 3 nanometers and 7 nanometers.

* * * * *